United States Patent
Morales et al.

(10) Patent No.: US 9,636,107 B2
(45) Date of Patent: May 2, 2017

(54) DEVICES AND METHODS FOR HEART VALVE REPAIR

(71) Applicant: Ancora Heart, Inc., Santa Clara, CA (US)

(72) Inventors: Rodolfo A. Morales, Los Gatos, CA (US); Niel F. Starksen, Los Altos Hills, CA (US)

(73) Assignee: Ancora Heart, Inc., Santa Clara, CA (US)

( * ) Notice: Subject to any disclaimer, the term of this patent is extended or adjusted under 35 U.S.C. 154(b) by 12 days.

(21) Appl. No.: 14/589,855

(22) Filed: Jan. 5, 2015

(65) Prior Publication Data

US 2015/0182216 A1 Jul. 2, 2015

Related U.S. Application Data

(60) Continuation of application No. 10/776,682, filed on Feb. 10, 2004, now abandoned, which is a division of
(Continued)

(51) Int. Cl.
*A61F 2/24* (2006.01)
*A61B 17/04* (2006.01)
(Continued)

(52) U.S. Cl.
CPC .......... *A61B 17/0487* (2013.01); *A61B 1/04* (2013.01); *A61B 8/12* (2013.01);
(Continued)

(58) Field of Classification Search
CPC .......... A61B 17/00234; A61B 17/0644; A61B 17/083; A61B 17/1285; A61B 17/3423;
(Continued)

(56) References Cited

U.S. PATENT DOCUMENTS 3,656,185 A 4/1972 Carpentier
3,773,034 A 11/1973 Burns et al.
(Continued)

FOREIGN PATENT DOCUMENTS

EP 0 637 431 A1 2/1995
EP 0 669 101 A1 8/1995
(Continued)

OTHER PUBLICATIONS

De Simone, R. et al. (Apr. 15, 1993). "Adjustable Tricuspid Valve Annuloplasty Assisted by Intraoperative Transesophageal Color Doppler Echocardiography," *Am. J. Cardiol.* 71(11):926-931.
(Continued)

*Primary Examiner* — Todd J Scherbel
*Assistant Examiner* — Son Dang

(57) ABSTRACT

Methods and devices provide constriction of a heart valve annulus to treat cardiac valve regurgitation and other conditions. Embodiments typically include a device for attaching a cinching or tightening apparatus to a heart valve annulus to reduce the circumference of the annulus, thus reducing valve regurgitation. Tightening devices may include multiple tethered clips, multiple untethered crimping clips, stabilizing devices, visualization devices, and the like. In one embodiment, a plurality of tethered clips is secured circumferentially to a valve annulus, and the tether coupling the clips is cinched to reduce the circumference of at least a portion of the annulus. Methods and devices may be used in open heart surgical procedures, minimally invasive procedures, catheter-based procedures, and/or procedures on beating hearts or stopped hearts.

7 Claims, 20 Drawing Sheets

Related U.S. Application Data application No. 10/461,043, filed on Jun. 13, 2003, now Pat. No. 6,986,775.

(60) Provisional application No. 60/388,935, filed on Jun. 13, 2002, provisional application No. 60/429,288, filed on Nov. 25, 2002, provisional application No. 60/445,890, filed on Feb. 6, 2003, provisional application No. 60/462,502, filed on Apr. 10, 2003.

(51) Int. Cl.

| | |
|---|---|
| A61B 17/00 | (2006.01) |
| A61B 17/064 | (2006.01) |
| A61B 17/068 | (2006.01) |
| A61B 17/08 | (2006.01) |
| A61B 17/10 | (2006.01) |
| A61B 17/128 | (2006.01) |
| A61B 17/34 | (2006.01) |
| A61B 1/04 | (2006.01) |
| A61B 8/12 | (2006.01) |
| A61B 17/06 | (2006.01) |
| A61B 1/00 | (2006.01) |

(52) U.S. Cl.
CPC .... *A61B 17/00234* (2013.01); *A61B 17/0401* (2013.01); *A61B 17/0644* (2013.01); *A61B 17/0684* (2013.01); *A61B 17/083* (2013.01); *A61B 17/10* (2013.01); *A61B 17/1285* (2013.01); *A61B 17/3421* (2013.01); *A61B 17/3423* (2013.01); *A61F 2/2445* (2013.01); *A61B 1/00082* (2013.01); *A61B 1/00096* (2013.01); *A61B 2017/00243* (2013.01); *A61B 2017/0488* (2013.01); *A61B 2017/0496* (2013.01); *A61B 2017/06023* (2013.01); *A61B 2017/3425* (2013.01); *A61B 2017/3484* (2013.01); *A61B 2017/3488* (2013.01); *A61F 2/2451* (2013.01)

(58) Field of Classification Search
CPC ... A61B 8/12; A61B 17/0401; A61B 17/0487; A61B 17/0684; A61B 17/10; A61B 17/3421; A61B 1/04; A61F 2/2445
See application file for complete search history.

(56) References Cited

U.S. PATENT DOCUMENTS

| | | |
|---|---|---|
| 3,961,419 A | 6/1976 | Schwartz |
| 3,976,079 A | 8/1976 | Samuels et al. |
| 4,014,492 A | 3/1977 | Rothfuss |
| 4,034,473 A | 7/1977 | May |
| 4,042,979 A | 8/1977 | Angell |
| 4,043,504 A | 8/1977 | Hueil et al. |
| 4,053,979 A | 10/1977 | Tuthill et al. |
| 4,055,861 A | 11/1977 | Carpentier et al. |
| 4,069,825 A | 1/1978 | Akiyama |
| 4,273,127 A | 6/1981 | Auth et al. |
| 4,290,151 A | 9/1981 | Massana |
| 4,384,406 A | 5/1983 | Tischlinger |
| 4,445,509 A | 5/1984 | Auth |
| 4,445,892 A | 5/1984 | Hussein et al. |
| 4,489,446 A | 12/1984 | Reed |
| 4,494,542 A | 1/1985 | Lee |
| 4,619,247 A | 10/1986 | Inoue et al. |
| 4,681,093 A | 7/1987 | Ono et al. |
| 4,700,250 A | 10/1987 | Kuriyama |
| 4,726,371 A | 2/1988 | Gibbens |
| 4,758,221 A | 7/1988 | Jureidini |
| 4,784,133 A | 11/1988 | Mackin |
| 4,845,851 A | 7/1989 | Warthen |
| 4,848,341 A | 7/1989 | Ahmad |
| 4,850,354 A | 7/1989 | McGurk-Burleson et al. |
| 4,961,738 A | 10/1990 | Mackin |
| 4,969,893 A | 11/1990 | Swor |
| 4,976,710 A | 12/1990 | Mackin |
| 5,053,047 A | 10/1991 | Yoon |
| 5,064,431 A | 11/1991 | Gilbertson et al. |
| 5,084,058 A | 1/1992 | Li |
| 5,103,804 A | 4/1992 | Abele et al. |
| 5,133,723 A | 7/1992 | Li et al. |
| 5,195,990 A | 3/1993 | Weldon |
| 5,221,255 A | 6/1993 | Mahurkar et al. |
| 5,242,456 A | 9/1993 | Nash et al. |
| 5,257,975 A | 11/1993 | Foshee |
| 5,312,341 A | 5/1994 | Turi |
| 5,324,298 A | 6/1994 | Phillips et al. |
| 5,344,439 A | 9/1994 | Otten |
| 5,346,500 A | 9/1994 | Suchart |
| 5,358,479 A | 10/1994 | Wilson |
| 5,364,407 A | 11/1994 | Poll |
| 5,366,479 A | 11/1994 | McGarry et al. |
| 5,368,564 A | 11/1994 | Savage |
| 5,368,591 A | 11/1994 | Lennox et al. |
| 5,383,905 A | 1/1995 | Golds et al. |
| 5,409,483 A | 4/1995 | Campbell et al. |
| 5,415,666 A | 5/1995 | Gourlay et al. |
| 5,417,700 A | 5/1995 | Egan |
| 5,423,837 A | 6/1995 | Mericle et al. |
| 5,437,680 A | 8/1995 | Yoon |
| 5,439,470 A | 8/1995 | Li |
| 5,450,860 A | 9/1995 | O'Connor |
| 5,452,513 A | 9/1995 | Zinnbauer et al. |
| 5,474,572 A | 12/1995 | Hayhurst |
| 5,507,725 A | 4/1996 | Savage et al. |
| 5,520,702 A | 5/1996 | Sauer et al. |
| 5,522,873 A | 6/1996 | Jackman et al. |
| 5,524,630 A | 6/1996 | Crowley |
| 5,527,323 A | 6/1996 | Jervis et al. |
| 5,545,134 A | 8/1996 | Hilaire et al. |
| 5,545,168 A | 8/1996 | Burke |
| 5,565,122 A | 10/1996 | Zinnbauer et al. |
| 5,571,215 A | 11/1996 | Sterman et al. |
| 5,591,194 A | 1/1997 | Berthiaume |
| 5,626,614 A | 5/1997 | Hart |
| 5,630,824 A | 5/1997 | Hart |
| 5,640,955 A | 6/1997 | Ockuly et al. |
| 5,643,289 A | 7/1997 | Sauer et al. |
| 5,669,917 A | 9/1997 | Sauer et al. |
| 5,674,279 A | 10/1997 | Wright et al. |
| 5,690,655 A | 11/1997 | Hart et al. |
| 5,695,505 A | 12/1997 | Yoon |
| 5,709,695 A | 1/1998 | Northrup, III |
| 5,713,950 A | 2/1998 | Cox |
| 5,716,370 A | 2/1998 | Williamson, IV et al. |
| 5,718,725 A | 2/1998 | Sterman et al. |
| 5,725,542 A | 3/1998 | Yoon |
| 5,735,290 A | 4/1998 | Sterman et al. |
| 5,741,260 A | 4/1998 | Songer et al. |
| 5,741,301 A | 4/1998 | Pagedas |
| 5,752,518 A | 5/1998 | McGee et al. |
| 5,752,964 A | 5/1998 | Mericle |
| 5,752,966 A | 5/1998 | Chang |
| 5,755,730 A | 5/1998 | Swain et al. |
| 5,766,189 A | 6/1998 | Matsuno |
| 5,766,240 A | 6/1998 | Johnson |
| 5,769,812 A | 6/1998 | Stevens et al. |
| 5,779,673 A | 7/1998 | Roth et al. |
| 5,779,718 A | 7/1998 | Green et al. |
| 5,807,403 A | 9/1998 | Beyar et al. |
| 5,810,848 A | 9/1998 | Hayhurst |
| 5,810,853 A | 9/1998 | Yoon |
| 5,817,107 A | 10/1998 | Schaller |
| 5,827,171 A | 10/1998 | Dobak, III et al. |
| 5,843,169 A | 12/1998 | Taheri |
| 5,848,969 A | 12/1998 | Panescu et al. |
| 5,849,035 A | 12/1998 | Pathak et al. |
| 5,860,992 A | 1/1999 | Daniel et al. |
| 5,860,993 A | 1/1999 | Thompson et al. |
| 5,861,003 A | 1/1999 | Latson et al. |
| 5,868,733 A | 2/1999 | Ockuly et al. |

(56) References Cited

U.S. PATENT DOCUMENTS

| | | |
|---|---|---|
| 5,879,371 A | 3/1999 | Gardiner et al. |
| 5,885,238 A | 3/1999 | Stevens et al. |
| 5,888,240 A | 3/1999 | Carpentier et al. |
| 5,902,321 A | 5/1999 | Caspari et al. |
| 5,904,651 A * | 5/1999 | Swanson .............. A61B 5/0084 600/342 |
| 5,906,579 A | 5/1999 | Vander Salm et al. |
| 5,919,208 A | 7/1999 | Valenti |
| 5,935,149 A | 8/1999 | Ek |
| 5,947,983 A | 9/1999 | Solar et al. |
| 5,961,440 A | 10/1999 | Schweich, Jr. et al. |
| 5,961,539 A | 10/1999 | Northrup, III et al. |
| 5,972,004 A | 10/1999 | Williamson, IV et al. |
| 5,984,933 A | 11/1999 | Yoon |
| 5,989,284 A | 11/1999 | Laufer |
| 5,991,650 A | 11/1999 | Swanson et al. |
| 6,010,531 A | 1/2000 | Donlon et al. |
| 6,013,083 A | 1/2000 | Bennett |
| 6,015,428 A | 1/2000 | Pagedas |
| 6,050,936 A | 4/2000 | Schweich, Jr. et al. |
| 6,056,743 A | 5/2000 | Ellis et al. |
| 6,059,715 A | 5/2000 | Schweich, Jr. et al. |
| 6,066,160 A | 5/2000 | Colvin et al. |
| 6,074,401 A | 6/2000 | Gardiner et al. |
| 6,077,214 A | 6/2000 | Mortier et al. |
| 6,077,989 A | 6/2000 | Kandel et al. |
| 6,080,182 A | 6/2000 | Shaw et al. |
| 6,099,553 A | 8/2000 | Hart et al. |
| 6,125,852 A | 10/2000 | Stevens et al. |
| 6,149,658 A | 11/2000 | Gardiner et al. |
| 6,162,168 A | 12/2000 | Schweich, Jr. et al. |
| 6,165,183 A | 12/2000 | Kuehn et al. |
| 6,197,017 B1 | 3/2001 | Brock et al. |
| 6,203,531 B1 | 3/2001 | Ockuly et al. |
| 6,210,432 B1 | 4/2001 | Solem et al. |
| 6,221,084 B1 | 4/2001 | Fleenor |
| 6,228,096 B1 | 5/2001 | Marchand |
| 6,250,308 B1 | 6/2001 | Cox |
| 6,254,620 B1 | 7/2001 | Koh et al. |
| 6,258,118 B1 | 7/2001 | Baum et al. |
| 6,260,552 B1 | 7/2001 | Mortier et al. |
| 6,269,819 B1 | 8/2001 | Oz et al. |
| 6,283,993 B1 | 9/2001 | Cosgrove et al. |
| 6,306,149 B1 | 10/2001 | Meade |
| 6,312,447 B1 | 11/2001 | Grimes |
| 6,328,727 B1 | 12/2001 | Frazier et al. |
| 6,332,893 B1 | 12/2001 | Mortier et al. |
| 6,355,030 B1 | 3/2002 | Aldrich et al. |
| 6,378,289 B1 | 4/2002 | Trudeau et al. |
| 6,391,048 B1 | 5/2002 | Ginn et al. |
| 6,406,420 B1 | 6/2002 | McCarthy et al. |
| 6,409,743 B1 | 6/2002 | Fenton, Jr. |
| 6,423,088 B1 | 7/2002 | Fenton, Jr. |
| 6,428,562 B2 | 8/2002 | Bonutti |
| 6,432,123 B2 | 8/2002 | Schwartz et al. |
| 6,461,327 B1 | 10/2002 | Addis et al. |
| 6,491,689 B1 | 12/2002 | Ellis et al. |
| 6,514,265 B2 | 2/2003 | Ho et al. |
| 6,524,338 B1 | 2/2003 | Gundry |
| 6,533,753 B1 | 3/2003 | Haarstad et al. |
| 6,540,755 B2 | 4/2003 | Ockuly et al. |
| 6,551,332 B1 | 4/2003 | Nguyen et al. |
| 6,575,971 B2 | 6/2003 | Hauck et al. |
| 6,589,160 B2 | 7/2003 | Schweich, Jr. et al. |
| 6,602,288 B1 | 8/2003 | Cosgrove et al. |
| 6,602,289 B1 | 8/2003 | Colvin et al. |
| 6,607,541 B1 | 8/2003 | Gardiner et al. |
| 6,613,059 B2 | 9/2003 | Schaller et al. |
| 6,619,291 B2 | 9/2003 | Hlavka et al. |
| 6,626,899 B2 | 9/2003 | Houser et al. |
| 6,629,534 B1 | 10/2003 | St. Goar et al. |
| 6,641,593 B1 | 11/2003 | Schaller et al. |
| 6,648,903 B1 | 11/2003 | Pierson, III |
| 6,651,671 B1 | 11/2003 | Donlon et al. |
| 6,655,386 B1 | 12/2003 | Makower et al. |
| 6,669,687 B1 | 12/2003 | Saadat |
| 6,676,702 B2 | 1/2004 | Mathis |
| 6,689,164 B1 | 2/2004 | Seguin |
| 6,699,263 B2 | 3/2004 | Cope |
| 6,702,826 B2 | 3/2004 | Liddicoat et al. |
| 6,716,243 B1 | 4/2004 | Colvin et al. |
| 6,718,985 B2 | 4/2004 | Hlavka et al. |
| 6,723,038 B1 | 4/2004 | Schroeder et al. |
| 6,723,107 B1 | 4/2004 | Skiba et al. |
| 6,733,509 B2 | 5/2004 | Nobles et al. |
| 6,752,813 B2 | 6/2004 | Goldfarb et al. |
| 6,790,231 B2 | 9/2004 | Liddicoat et al. |
| 6,793,618 B2 | 9/2004 | Schweich, Jr. et al. |
| 6,818,001 B2 | 11/2004 | Wulfman et al. |
| 6,908,424 B2 | 6/2005 | Mortier et al. |
| 6,923,818 B2 | 8/2005 | Muramatsu et al. |
| 6,932,792 B1 | 8/2005 | St. Goar et al. |
| 6,951,557 B2 | 10/2005 | Ellis et al. |
| 6,986,775 B2 | 1/2006 | Morales et al. |
| 6,991,643 B2 | 1/2006 | Saadat |
| 6,997,931 B2 | 2/2006 | Sauer et al. |
| 7,004,958 B2 | 2/2006 | Adams et al. |
| 7,037,334 B1 | 5/2006 | Hlavka et al. |
| 7,048,754 B2 | 5/2006 | Martin et al. |
| 7,101,395 B2 | 9/2006 | Tremulis et al. |
| 7,125,421 B2 | 10/2006 | Tremulis et al. |
| 7,166,127 B2 | 1/2007 | Spence et al. |
| 7,186,262 B2 | 3/2007 | Saadat |
| 7,189,199 B2 | 3/2007 | McCarthy et al. |
| 7,235,086 B2 | 6/2007 | Sauer et al. |
| 7,241,310 B2 | 7/2007 | Taylor et al. |
| 7,257,450 B2 | 8/2007 | Auth et al. |
| 7,326,231 B2 | 2/2008 | Phillips et al. |
| 7,331,972 B1 | 2/2008 | Cox |
| 7,344,544 B2 | 3/2008 | Bender et al. |
| 7,452,325 B2 | 11/2008 | Schaller |
| 7,534,204 B2 | 5/2009 | Starksen et al. |
| 7,588,582 B2 | 9/2009 | Starksen et al. |
| 7,618,449 B2 | 11/2009 | Tremulis et al. |
| 7,666,193 B2 | 2/2010 | Starksen et al. |
| 7,740,638 B2 | 6/2010 | Hyde |
| 7,753,858 B2 | 7/2010 | Starksen et al. |
| 7,753,924 B2 | 7/2010 | Starksen et al. |
| 7,766,812 B2 | 8/2010 | Schroeder et al. |
| 7,832,406 B2 | 11/2010 | Ellis et al. |
| 7,850,600 B1 | 12/2010 | Piskun |
| 7,883,538 B2 | 2/2011 | To et al. |
| 7,918,787 B2 | 4/2011 | Saadat |
| 8,287,555 B2 | 10/2012 | Starksen et al. |
| 8,343,173 B2 | 1/2013 | Starksen et al. |
| 2001/0005787 A1 | 6/2001 | Oz et al. |
| 2001/0014800 A1 | 8/2001 | Frazier et al. |
| 2001/0023332 A1 | 9/2001 | Hahnen |
| 2001/0031979 A1 | 10/2001 | Ricci |
| 2001/0047165 A1 | 11/2001 | Makower et al. |
| 2002/0007190 A1 | 1/2002 | Wulfman et al. |
| 2002/0013571 A1 | 1/2002 | Goldfarb et al. |
| 2002/0013621 A1 | 1/2002 | Stobie et al. |
| 2002/0026201 A1 | 2/2002 | Foerster et al. |
| 2002/0029080 A1 | 3/2002 | Mortier et al. |
| 2002/0035361 A1 | 3/2002 | Houser et al. |
| 2002/0042621 A1 | 4/2002 | Liddicoat et al. |
| 2002/0065536 A1 | 5/2002 | Hart et al. |
| 2002/0072757 A1 | 6/2002 | Ahmed et al. |
| 2002/0077524 A1 | 6/2002 | Schweich, Jr. et al. |
| 2002/0087048 A1 | 7/2002 | Brock et al. |
| 2002/0087049 A1 | 7/2002 | Brock et al. |
| 2002/0087148 A1 | 7/2002 | Brock et al. |
| 2002/0087169 A1 * | 7/2002 | Brock .................... A61B 90/36 606/139 |
| 2002/0095167 A1 | 7/2002 | Liddicoat et al. |
| 2002/0095175 A1 | 7/2002 | Brock et al. |
| 2002/0138044 A1 | 9/2002 | Streeter et al. |
| 2002/0156526 A1 | 10/2002 | Hlavka et al. |
| 2002/0161378 A1 | 10/2002 | Downing |
| 2002/0165486 A1 | 11/2002 | Bertolero et al. |
| 2002/0173841 A1 | 11/2002 | Ortiz et al. |
| 2002/0183787 A1 | 12/2002 | Wahr et al. |
| 2002/0183835 A1 | 12/2002 | Taylor et al. |

(56) References Cited

U.S. PATENT DOCUMENTS

| | | |
|---|---|---|
| 2002/0193815 A1 | 12/2002 | Foerster et al. |
| 2002/0198536 A1 | 12/2002 | Trout, III et al. |
| 2003/0009196 A1 | 1/2003 | Peterson |
| 2003/0014060 A1* | 1/2003 | Wilson, Jr. ......... A61B 17/1285 606/142 |
| 2003/0018358 A1 | 1/2003 | Saadat |
| 2003/0032979 A1 | 2/2003 | Mortier et al. |
| 2003/0033006 A1 | 2/2003 | Phillips et al. |
| 2003/0045893 A1 | 3/2003 | Ginn |
| 2003/0060813 A1 | 3/2003 | Loeb et al. |
| 2003/0069593 A1 | 4/2003 | Tremulis et al. |
| 2003/0078603 A1 | 4/2003 | Schaller et al. |
| 2003/0093118 A1 | 5/2003 | Ho et al. |
| 2003/0105520 A1 | 6/2003 | Alferness et al. |
| 2003/0125739 A1 | 7/2003 | Bagga et al. |
| 2003/0125767 A1 | 7/2003 | Collier et al. |
| 2003/0130731 A1 | 7/2003 | Vidlund et al. |
| 2003/0144697 A1 | 7/2003 | Mathis et al. |
| 2003/0158464 A1 | 8/2003 | Bertolero |
| 2003/0158581 A1 | 8/2003 | Levinson |
| 2003/0167062 A1 | 9/2003 | Gambale et al. |
| 2003/0167071 A1 | 9/2003 | Martin et al. |
| 2003/0171776 A1 | 9/2003 | Adams et al. |
| 2003/0199974 A1 | 10/2003 | Lee et al. |
| 2003/0220685 A1 | 11/2003 | Hlvaka et al. |
| 2003/0225420 A1 | 12/2003 | Wardle |
| 2003/0233105 A1 | 12/2003 | Gayton |
| 2003/0233142 A1 | 12/2003 | Morales et al. |
| 2003/0236535 A1 | 12/2003 | Onuki et al. |
| 2004/0003819 A1 | 1/2004 | St. Goar et al. |
| 2004/0019378 A1 | 1/2004 | Hlavka et al. |
| 2004/0024414 A1 | 2/2004 | Downing |
| 2004/0030382 A1 | 2/2004 | St. Goar et al. |
| 2004/0039442 A1 | 2/2004 | St. Goar et al. |
| 2004/0097788 A1 | 5/2004 | Mourlas et al. |
| 2004/0122450 A1 | 6/2004 | Oren et al. |
| 2004/0152947 A1 | 8/2004 | Schroeder et al. |
| 2004/0172046 A1 | 9/2004 | Hlavka et al. |
| 2004/0181238 A1 | 9/2004 | Zarbatany et al. |
| 2004/0186378 A1 | 9/2004 | Gesswein |
| 2004/0193191 A1 | 9/2004 | Starksen et al. |
| 2004/0204724 A1 | 10/2004 | Kissel et al. |
| 2004/0210238 A1 | 10/2004 | Nobles et al. |
| 2004/0236372 A1 | 11/2004 | Anspach, III et al. |
| 2004/0236419 A1 | 11/2004 | Milo |
| 2004/0243227 A1 | 12/2004 | Starksen et al. |
| 2005/0055052 A1 | 3/2005 | Lombardo et al. |
| 2005/0055087 A1 | 3/2005 | Starksen |
| 2005/0065550 A1 | 3/2005 | Starksen et al. |
| 2005/0075654 A1 | 4/2005 | Kelleher |
| 2005/0075723 A1 | 4/2005 | Schroeder et al. |
| 2005/0080454 A1 | 4/2005 | Drews et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0119523 A1 | 6/2005 | Starksen et al. |
| 2005/0119673 A1 | 6/2005 | Gordon et al. |
| 2005/0137689 A1 | 6/2005 | Salahieh et al. |
| 2005/0184122 A1 | 8/2005 | Hlavka et al. |
| 2005/0192629 A1 | 9/2005 | Saadat et al. |
| 2005/0197694 A1 | 9/2005 | Pai et al. |
| 2005/0209690 A1 | 9/2005 | Mathis et al. |
| 2005/0216078 A1 | 9/2005 | Starksen et al. |
| 2005/0228452 A1 | 10/2005 | Mourlas et al. |
| 2005/0251157 A1 | 11/2005 | Saadat et al. |
| 2005/0251159 A1 | 11/2005 | Ewers et al. |
| 2005/0251166 A1 | 11/2005 | Vaughan et al. |
| 2005/0251177 A1 | 11/2005 | Saadat et al. |
| 2005/0251205 A1 | 11/2005 | Ewers et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0273138 A1 | 12/2005 | To et al. |
| 2005/0277966 A1 | 12/2005 | Ewers et al. |
| 2005/0277981 A1 | 12/2005 | Maahs et al. |
| 2005/0277983 A1 | 12/2005 | Saadat et al. |
| 2006/0025750 A1 | 2/2006 | Starksen et al. |
| 2006/0025784 A1 | 2/2006 | Starksen et al. |
| 2006/0025787 A1 | 2/2006 | Morales et al. |
| 2006/0058817 A1 | 3/2006 | Starksen et al. |
| 2006/0069429 A1 | 3/2006 | Spence et al. |
| 2006/0122633 A1 | 6/2006 | To et al. |
| 2006/0129188 A1 | 6/2006 | Starksen et al. |
| 2006/0161040 A1 | 7/2006 | McCarthy et al. |
| 2006/0178682 A1 | 8/2006 | Boehlke |
| 2006/0184203 A1 | 8/2006 | Martin et al. |
| 2006/0190030 A1 | 8/2006 | To et al. |
| 2006/0229708 A1 | 10/2006 | Powell et al. |
| 2006/0241656 A1 | 10/2006 | Starksen et al. |
| 2006/0264975 A1 | 11/2006 | Pipenhagen et al. |
| 2006/0270976 A1 | 11/2006 | Savage et al. |
| 2006/0271101 A1 | 11/2006 | Saadat et al. |
| 2006/0287661 A1 | 12/2006 | Bolduc et al. |
| 2007/0005081 A1 | 1/2007 | Findlay, III et al. |
| 2007/0005394 A1 | 1/2007 | Bleyendaal et al. |
| 2007/0010857 A1 | 1/2007 | Sugimoto et al. |
| 2007/0032820 A1 | 2/2007 | Chin-Chen et al. |
| 2007/0038293 A1 | 2/2007 | St. Goar et al. |
| 2007/0049942 A1 | 3/2007 | Hindrichs et al. |
| 2007/0051377 A1 | 3/2007 | Douk et al. |
| 2007/0055206 A1 | 3/2007 | To et al. |
| 2007/0093805 A1 | 4/2007 | Auth et al. |
| 2007/0112244 A1 | 5/2007 | McCarthy et al. |
| 2007/0112422 A1 | 5/2007 | Dehdashtian |
| 2007/0112424 A1 | 5/2007 | Spence et al. |
| 2008/0045977 A1 | 2/2008 | To et al. |
| 2008/0045982 A1 | 2/2008 | To et al. |
| 2008/0045983 A1 | 2/2008 | To et al. |
| 2008/0051810 A1 | 2/2008 | To et al. |
| 2008/0051832 A1 | 2/2008 | To et al. |
| 2008/0051837 A1 | 2/2008 | To et al. |
| 2008/0058765 A1 | 3/2008 | Jais et al. |
| 2008/0058868 A1 | 3/2008 | To et al. |
| 2008/0097489 A1 | 4/2008 | Goldfarb et al. |
| 2008/0103439 A1 | 5/2008 | Torrance et al. |
| 2008/0119882 A1 | 5/2008 | Cox |
| 2008/0172035 A1 | 7/2008 | Starksen et al. |
| 2008/0177380 A1 | 7/2008 | Starksen et al. |
| 2008/0228032 A1 | 9/2008 | Starksen et al. |
| 2008/0234701 A1 | 9/2008 | Morales et al. |
| 2008/0234702 A1 | 9/2008 | Morales et al. |
| 2008/0234704 A1 | 9/2008 | Starksen et al. |
| 2008/0234728 A1 | 9/2008 | Starksen et al. |
| 2008/0234815 A1 | 9/2008 | Starksen |
| 2008/0243150 A1 | 10/2008 | Starksen et al. |
| 2008/0294177 A1 | 11/2008 | To et al. |
| 2009/0182417 A1 | 7/2009 | Tremulis et al. |
| 2009/0222083 A1 | 9/2009 | Nguyen et al. |
| 2009/0234318 A1 | 9/2009 | Loulmet et al. |
| 2009/0276038 A1 | 11/2009 | Tremulis et al. |
| 2010/0023056 A1 | 1/2010 | Johansson et al. |
| 2010/0049213 A1 | 2/2010 | Serina et al. |
| 2010/0076408 A1 | 3/2010 | Krever et al. |
| 2010/0076548 A1 | 3/2010 | Konno |
| 2010/0082098 A1 | 4/2010 | Starksen et al. |
| 2010/0094213 A1 | 4/2010 | Horn et al. |
| 2010/0094314 A1 | 4/2010 | Hernlund et al. |
| 2010/0121349 A1 | 5/2010 | Meier et al. |
| 2010/0185172 A1 | 7/2010 | Fabro |
| 2010/0198056 A1 | 8/2010 | Fabro et al. |
| 2010/0198192 A1 | 8/2010 | Serina et al. |
| 2010/0198208 A1 | 8/2010 | Napp et al. |
| 2013/0304093 A1 | 11/2013 | Serina et al. |
| 2014/0142619 A1 | 5/2014 | Serina et al. |

FOREIGN PATENT DOCUMENTS

| | | |
|---|---|---|
| JP | 6-237939 A | 8/1994 |
| JP | 9-289989 A | 11/1997 |
| JP | 10-506812 A | 7/1998 |
| JP | 11-318910 A | 11/1999 |
| JP | 2000-505336 A | 5/2000 |
| JP | 2001-500749 A | 1/2001 |

(56) References Cited

FOREIGN PATENT DOCUMENTS

| | | |
|---|---|---|
| JP | 2004-500170 A | 1/2004 |
| JP | 2004-321343 A | 11/2004 |
| JP | 2005-021576 A | 1/2005 |
| WO | WO-94/03227 A1 | 2/1994 |
| WO | WO-95/15715 A1 | 6/1995 |
| WO | WO-96/08208 A1 | 3/1996 |
| WO | WO-96/10365 A1 | 4/1996 |
| WO | WO-96/39942 A1 | 12/1996 |
| WO | WO-97/27799 A1 | 8/1997 |
| WO | WO-97/27807 A1 | 8/1997 |
| WO | WO-97/29709 A1 | 8/1997 |
| WO | WO-97/30638 A1 | 8/1997 |
| WO | WO-98/07375 A1 | 2/1998 |
| WO | WO-99/59477 A1 | 11/1999 |
| WO | WO-00/60995 A2 | 10/2000 |
| WO | WO-00/60995 A3 | 10/2000 |
| WO | WO-00/67640 A2 | 11/2000 |
| WO | WO-00/67640 A3 | 11/2000 |
| WO | WO-01/26586 A1 | 4/2001 |
| WO | WO-01/37742 A2 | 5/2001 |
| WO | WO-01/37742 A3 | 5/2001 |
| WO | WO-01/54618 A1 | 8/2001 |
| WO | WO-02/00099 A2 | 1/2002 |
| WO | WO-02/00099 A3 | 1/2002 |
| WO | WO-02/03892 A1 | 1/2002 |
| WO | WO-02/051329 A1 | 7/2002 |
| WO | WO-02/053011 A2 | 7/2002 |
| WO | WO-02/053011 A3 | 7/2002 |
| WO | WO-02/085251 A1 | 10/2002 |
| WO | WO-02/085252 A1 | 10/2002 |
| WO | WO-03/088875 A1 | 10/2003 |
| WO | WO-03/097931 A1 | 11/2003 |
| WO | WO-03/105667 A2 | 12/2003 |
| WO | WO-03/105667 A3 | 12/2003 |
| WO | WO-03/105670 A2 | 12/2003 |
| WO | WO-03/105670 A3 | 12/2003 |
| WO | WO-2004/037317 A2 | 5/2004 |
| WO | WO-2004/037317 A3 | 5/2004 |
| WO | WO-2004/082523 A2 | 9/2004 |
| WO | WO-2004/082523 A3 | 9/2004 |
| WO | WO-2004/082538 A2 | 9/2004 |
| WO | WO-2004/082538 A3 | 9/2004 |
| WO | WO-2005/025644 A2 | 3/2005 |
| WO | WO-2004/082538 A3 | 7/2005 |
| WO | WO-2005/062931 A2 | 7/2005 |
| WO | WO-2005/102181 A1 | 11/2005 |
| WO | WO-2006/037073 A2 | 4/2006 |
| WO | WO-2006/097931 A2 | 9/2006 |
| WO | WO-2006/097931 A3 | 9/2006 |
| WO | WO-2006/116558 A2 | 11/2006 |
| WO | WO-2006/116558 A3 | 11/2006 |
| WO | WO-2006/116558 C2 | 11/2006 |
| WO | WO-2007/005495 A1 | 1/2007 |
| WO | WO-2007/021564 A1 | 2/2007 |
| WO | WO-2007/021834 A1 | 2/2007 |
| WO | WO-2007/035449 A2 | 3/2007 |
| WO | WO-2007/056502 A1 | 5/2007 |
| WO | WO-2007/100409 A2 | 9/2007 |
| WO | WO-2008/028135 A | 3/2008 |
| WO | WO-2008/028135 A3 | 3/2008 |
| WO | WO-2008/042987 A2 | 4/2008 |
| WO | WO-2008/042987 A3 | 4/2008 |
| WO | WO-2010/085457 A1 | 7/2010 |

OTHER PUBLICATIONS

De Simone, R. et al. (Apr. 1, 1994). "Adjustable Annuloplasty for Tricuspid Insufficiency with External Control," Reader's Comments and Reply, *Am. J. Cardiol.* 73(9):721-722.

Downing, S.W. et al. (2002). "Feasibility of Off-Pump ASD Closure Using Real-Time 3-D Echocardiography," *The Heart Surgery Forum* 5(2):96-99, Abstract 7025.
Final Office Action mailed on Dec. 26, 2007, for U.S. Appl. No. 10/776,682, filed Feb. 10, 2004, 6 pages.
Final Office Action mailed on Jan. 12, 2009, for U.S. Appl. No. 10/776,682, filed Feb. 10, 2004, 8 pages.
Final Office Action mailed on Oct. 22, 2010, for U.S. Appl. No. 10/776,682, filed Feb. 10, 2004, 10 pages.
Final Office Action mailed on May 11, 2010, for U.S. Appl. No. 11/237,461, filed Sep. 27, 2005, 6 pages.
Final Office Action mailed on Nov. 22, 2010, for U.S. Appl. No. 11/237,461, filed Sep. 27, 2005, 5 pages.
Final Office Action mailed on Aug. 5, 2014, for U.S. Appl. No. 10/776,682, filed Feb. 10, 2004, 7 pages.
International Search Report mailed on Feb. 3, 2004, for PCT Application No. PCT/US2003/018874, filed on Jun. 13, 2003, 3 pages.
International Search Report mailed Dec. 19, 2006, for PCT Application No. PCT/US2006/031190, filed Aug. 10, 2006, 3 pages.
International Search Report mailed on Apr. 2, 2007, for PCT Application No. PCT/US2006/043597, filed Nov. 8, 2006, 4 pages.
International Search Report mailed on Mar. 19, 2010, for PCT Patent Application No. PCT/US2010/021437, filed on Jan. 19, 2010, 1 page.
Nagy, Z.L. et al. (Dec. 2000). "Mitral Annuloplasty with a Suture Technique," *European Journal of Cardio-thoracic Surgery* 18(6):739-740.
Non-Final Office Action mailed on Oct. 23, 2006, for U.S. Appl. No. 10/776,682, filed Feb. 10, 2004, 14 pages.
Non-Final Office Action mailed on Nov. 30, 2006, for U.S. Appl. No. 10/776,682, filed Feb. 10, 2004, 14 pages.
Non-Final Office Action mailed on Aug. 6, 2008, for U.S. Appl. No. 10/776,682, filed Feb. 10, 2004, 7 pages.
Non-Final Office Action mailed on Mar. 31, 2009, for U.S. Appl. No. 11/237,461, filed Sep. 27, 2005, 6 pages.
Non-Final Office Action mailed on Jul. 6, 2009, for U.S. Appl. No. 10/776,682, filed Feb. 10, 2004, 9 pages.
Non-Final Office Action mailed on Oct. 2, 2009, for U.S. Appl. No. 11/237,461, filed Sep. 27, 2005, 7 pages.
Non-Final Office Action mailed on Apr. 15, 2010, for U.S. Appl. No. 10/776,682, filed Feb. 10, 2004, 9 pages.
Non-Final Office Action mailed on Jun. 7, 2010, for U.S. Appl. No. 11/237,461, filed Sep. 27, 2005, 8 pages.
Non-Final Office Action mailed on Nov. 17, 2010, for U.S. Appl. No. 12/131,841, filed Jun. 2, 2008, 10 pages.
Non-Final Office Action mailed on Feb. 11, 2011, for U.S. Appl. No. 12/132,328, filed Jun. 3, 2008, 9 pages.
Non-Final Office Action mailed on Oct. 18, 2011, for U.S. Appl. No. 10/776,682, filed Feb. 10, 2004, 7 pages.
Non-Final Office Action mailed on Oct. 3, 2013, for U.S. Appl. No. 10/776,682, filed Feb. 10, 2004, 7 pages.
Non-Final Office Action mailed on Nov. 24, 2015, for U.S. Appl. No. 14/156,347, filed Jan. 15, 2014, 5 pages.
Notice of Allowance mailed on Jun. 15, 2016, for U.S. Appl. No. 14/156,347, filed Jan. 15, 2014, 7 pages.
Shumay, S.J. et al. (Dec. 1988). "A 'Designer' Annuloplasty Ring for Patients with Massive Mitral Annular Dilatation," Ann. Thorac. Surg. 46(6):695-696.
Supplementary European Search Report mailed on Apr. 4, 2011, for EP Patent Application No. 03739139.8, filed on Jun. 13, 2003, 3 pages.
Towne, W.D. (Jan. 1973). "Letter to the Editor: Classification of Chordae Tendineae," *Circulation* 47:209.
U.S. Appl. No. 61/160,670, filed Mar. 16, 2009, by Fabro et al.
U.S. Appl. No. 61/083,109, filed Jul. 23, 2008, by Johansson.
U.S. Appl. No. 61/104,681, filed Oct. 10, 2008, by Serina et al.
U.S. Appl. No. 61/104,686, filed Oct. 10, 2008, by To et al.
U.S. Appl. No. 61/145,964, filed Jan. 20, 2009, by Fabro, Mariel.
U.S. Appl. No. 61/160,018, filed Mar. 13, 2009, by Johansson, Peter.

\* cited by examiner

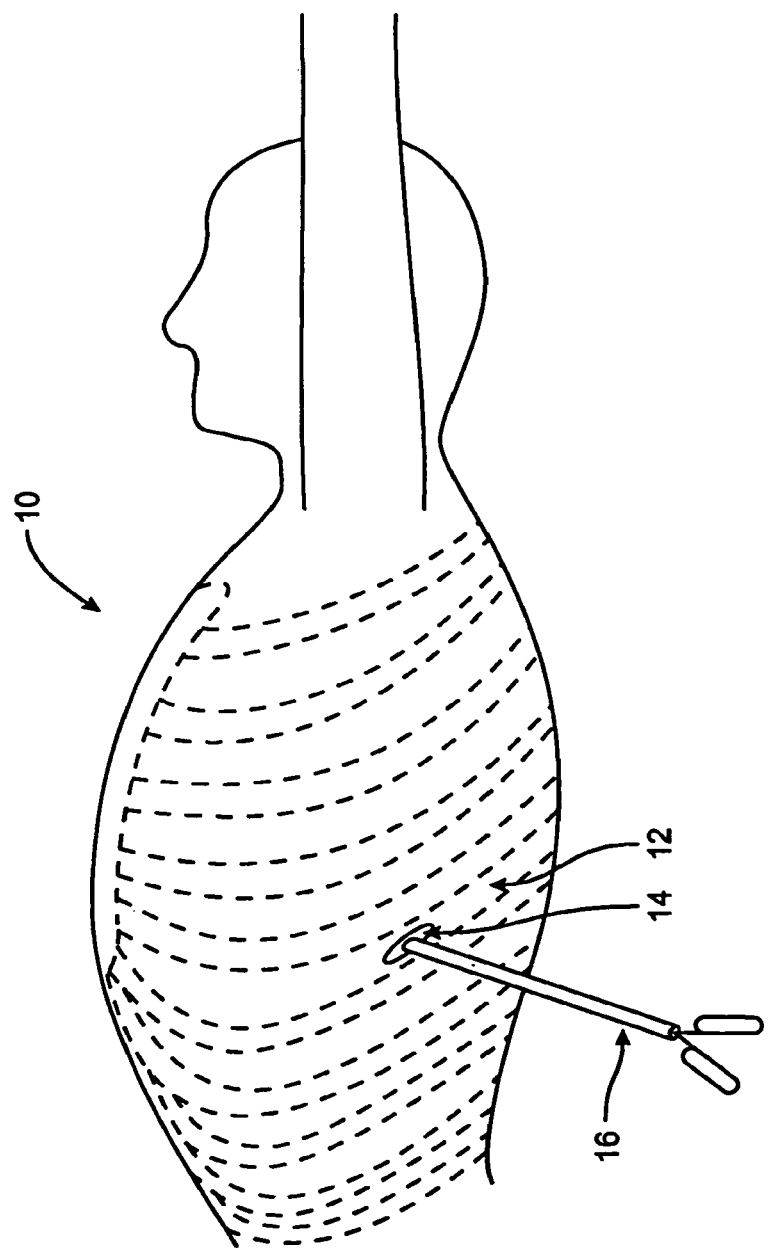

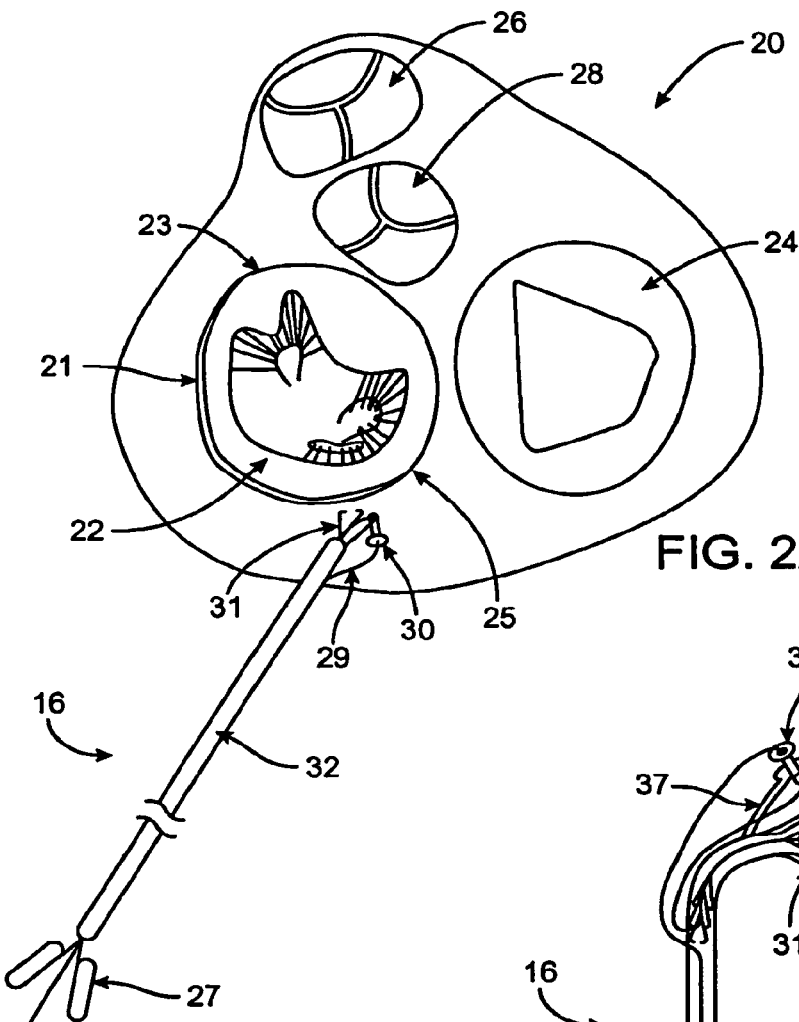
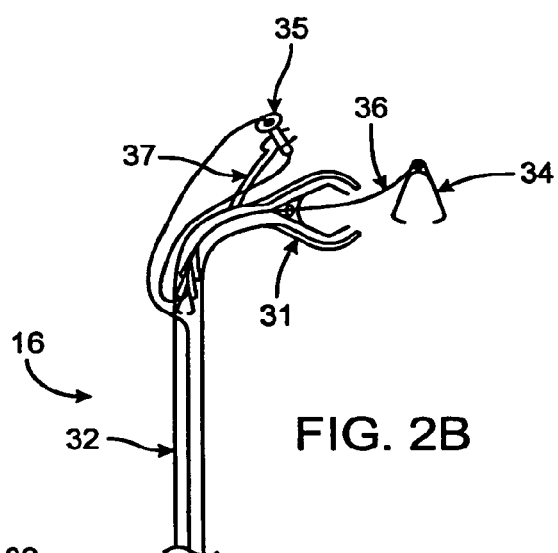
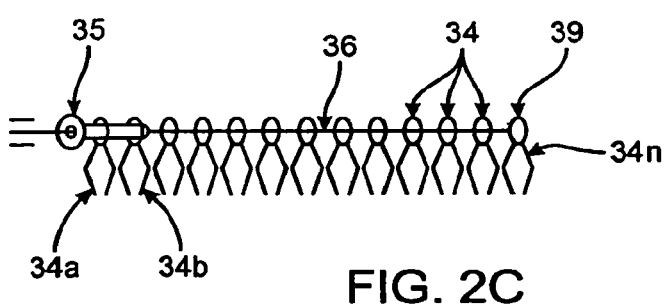
FIG. 2A
FIG. 2B
FIG. 2C

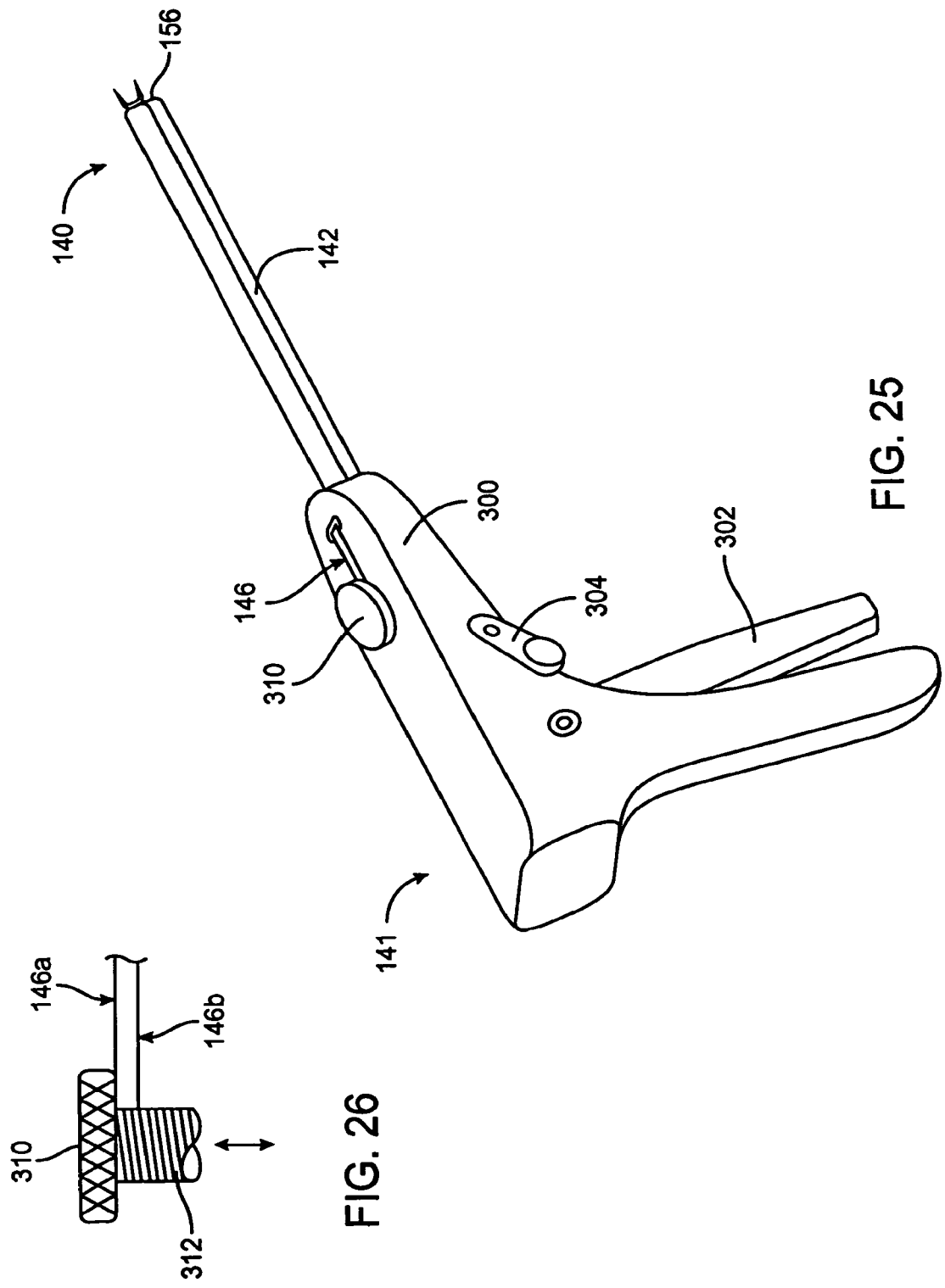

DEVICES AND METHODS FOR HEART VALVE REPAIR

CROSS-REFERENCES TO RELATED APPLICATIONS

This application is a continuation of, and claims the benefit of priority from U.S. patent application Ser. No. 10/776,682, filed on Feb. 10, 2004, which is a division of, and claims the benefit of priority from U.S. patent application Ser. No. 10/461,043, filed Jun. 13, 2003, now issued as U.S. Pat. No. 6,986,775, which claimed the benefit under 35 USC 119(e) of U.S. Provisional Application Nos. 60/388,935, filed on Jun. 13, 2002; 60/429,288, filed on Nov. 25, 2002; 60/445,890, filed on Feb. 6, 2003, and 60/462,502, filed on Apr. 10, 2003, the full disclosures of which are incorporated herein by reference.

BACKGROUND OF THE INVENTION

1. Field of the Invention

The present invention relates generally to medical methods and devices. More particularly, the invention relates to methods and devices for circulatory valve repair, especially for the repair of heart valves, such as repair of the mitral or tricuspid valve for treating mitral or tricuspid regurgitation.

Four valves in the heart direct blood flow through the heart in a forward direction. On the left side of the heart, the mitral and aortic valves direct oxygenated blood from the lungs to the aorta for distribution to the body. On the right side of the heart, the tricuspid and pulmonary valves direct de-oxygenated blood from the body to the pulmonary arteries for distribution to the lungs.

The four heart valves consist of moveable leaflets that open and close in response to differential pressures on either side of the valve. The mitral valve, for example, has two leaflets while the tricuspid valve has three. The components of the mitral valve assembly include a mitral valve annulus, an anterior leaflet, a posterior leaflet, two papillary muscles which are attached at their bases to the interior surface of the left ventricular wall, and multiple chordae tendineae, which are cord-like structures that couple the mitral valve leaflets to the papillary muscles. The other heart valves have similar supporting structures, though each is somewhat unique.

If a functional problem occurs in one or more heart valves, cardiac function is often adversely affected. Such valve problems may be classified as either stenosis, in which a valve does not open properly, or insufficiency (also known as regurgitation), in which a valve does not close properly. Mitral regurgitation, for example, is typically caused by dysfunction of the mitral annulus, subvalvular apparatus, or direct injury to the valve leaflets. Severe mitral regurgitation is a serious problem which, if left untreated, can adversely affect cardiac function and compromise a patient's quality of life and longevity. In cases where an atrioventricular valve becomes regurgitant due to damage to the valve supporting structures, papillary muscles, leaflets or annular geometry, the fraction of blood in the ventricle that is actually moved forward with each beat is reduced. To compensate, the ventricular cavity enlarges in an attempt to maintain forward output. By enlarging, the heart attempts to maintain the same absolute volume of forward flow by ejecting a reduced percentage of a larger volume. This enlargement of the ventricle is accompanied by an enlargement of the supporting structures and annulus of the valve, resulting in separation of the valve leaflets at their point of co-aptation during ventricular systole and further leaking of blood retrograde across the valve. This continues the cycle of ventricular enlargement, annular dilatation and regurgitation and subsequent loss of forward output and progressive heart failure. Other heart valve problems often cause similarly grave sequelae.

Treatment of heart valve stenosis or regurgitation, such as mitral or tricuspid regurgitation, often involves an open-heart surgical procedure to replace or repair the valve. Repair of a regurgitant valve such as the mitral valve is often performed in preference to replacement. Such procedures generally require a large incision into the thorax of the patient (a thoracotomy), sometimes requiring a median sternotomy (cutting through the middle of the sternum). Such procedures routinely include a corrective procedure called an annuloplasty, designed to restore the valve annulus shape, strengthen the annulus, and allow better leaflet co-aptation as a part of the repair. Such open heart procedures also usually involve placing the patient on a cardiopulmonary bypass machine for sustained periods so that the patient's heart and lungs can be artificially stopped during the procedure. Finally, valve repair and replacement procedures are typically technically challenging and require that a relatively large incision be made through the wall of the heart to access the valve. Due to the highly invasive nature of open heart valve repair or replacement, many patients, such as elderly patients, patients having recently undergone other surgical procedures, patients with comorbid medical conditions, children, late-stage heart failure patients and the like, are often considered too high-risk to undergo heart valve surgery and are committed to progressive deterioration and cardiac enlargement. Often, such patients have no feasible alternative treatments for their heart valve conditions.

Therefore, it would be advantageous to have methods and devices for repairing a mitral valve to treat mitral regurgitation in a less invasive manner than is available through current techniques. In some instances, it may be advantageous to provide for repair of a mitral valve, as well as other heart valves, through minimally invasive incisions or intravascularly. In other cases, it may be beneficial to use improved devices and methods in an open heart surgical procedure, on either a beating heart or a stopped heart. In beating heart procedures, including both minimally invasive and intravascular access procedures, it would be useful to provide for stabilization of the valve annulus while any procedure is being performed. In such beating heart procedures, it would be further useful to provide systems for the direct observation of the valve annulus from within a heart chamber to facilitate performing desired interventions. Moreover, it would be still further desirable if the apparatus and systems of the present invention were useful for treating not only the annulus of heart valves, but also other natural and created holes in tissue which require strengthening or closing. Improved devices and methods would ideally be relatively simple and easy to use and would enable durable, long-lasting mitral valve repair, either in a minimally invasive or open heart procedure, for many patients who are not candidates for more conventional procedures. At least some of these objectives will be met by the present invention.

2. Description of the Background Art

Published U.S. Application 2002/0163784A12 describes a port for providing access to a beating heart to perform diagnostic and therapeutic procedures, including a stapled annuloplasty procedure. Published U.S. Application 2002/0042621 describes a heart valve annuloplasty system with constrictable plication bands which are optionally attached to a linkage strip. Published U.S. Application 2002/0087169 describes a remote controlled catheter system which can be used to deliver anchors and a tether for performing an annuloplasty procedure. Other patent publications of interest include WO01/26586; US2001/0005787; US2001/0014800; US2002/0013621; US2002/0029080; US2002/0035361; US2002/0042621; US2002/0095167; and US2003/0074012. U.S. Pat. Nos. of interest include 4,014,492; 4,042,979; 4,043,504; 4,055,861; 4,700,250; 5,366,479; 5,450,860; 5,571,215; 5,674,279; 5,709,695; 5,752,518; 5,848,969; 5,860,992; 5,904,651; 5,961,539; 5,972,004; 6,165,183; 6,197,017; 6,250,308; 6,260,552; 6,283,993; 6,269,819; 6,312,447; 6,332,893; and 6,524,338. Publications of interest include De Simone et al. (1993) *Am. J. Cardiol.* 73:721-722 and Downing et al. (2001) *Heart Surgery Forum*, Abstract 7025.

BRIEF SUMMARY OF THE INVENTION

Methods and devices provide heart valve repair for mitral valve regurgitation and other heart valve conditions. Embodiments typically include a device for attaching a cinching or tightening apparatus to a heart valve annulus to reduce the circumference of the annulus, thus reducing valve regurgitation. Tightening devices include multiple tethered clips, multiple tethered or untethered crimping (deformable) clips, apparatus for delivering such clips, apparatus for selectively deforming clips onto the tether, systems for stabilizing the valve annulus during interventions, systems for viewing the valve annulus during an intervention, and the like.

As used hereinafter, the term "clips" is intended to refer to a wide variety of tissue anchors or fasteners which are able to (1) penetrate and fix to tissue, particularly into the fibrous tissue of a heart valve annulus and (2) provide for a secure attachment to a tether. Usually, the clips will initially be slidably received over the tether, e.g., through eyelets as described in greater detail hereinafter. Particular ones of the clips, however, may be fixedly secured to the tether even at the outset of the procedure. For example, often at least a first clip will be fixed to a lead end of the tether, where the first clip will be initially deployed into the annulus and will serve as an anchor at one end of the tether which is deployed about the annulus. Usually the remaining clips, including a series of intermediate clips and at least one terminal clip, will remain slidably secured over the tether until one of more of those clips is crimped or otherwise fixed to the tether during the interventions, as described in more detail below.

While the methods of the present invention are directed particularly at constricting a valve annulus, particularly for the treatment of valve regurgitation, the apparatus of the present invention may find broader applications. In particular, the clip deploying apparatus of the present invention may be used whenever it is desired to deliver a plurality of sequential clips, either in a straight line or in a curved line, in order to tighten tissue or optional to tether portions of tissue which are separate or which have been traumatically severed. Thus, the apparatus claimed herein are not meant to be limited in any way by the exemplary methods in which they are being used.

Generally, in accordance with the principles of the present invention, a plurality of tethered clips is secured circumferentially to a valve annulus, and the tether coupling the clips is cinched to reduce the circumference of at least a portion of the annulus. Optionally, at least a terminal clip may be deformed, such as by crimping, to secure the clip(s) to the tether, and the tether may pass through one, two or more eyelets on each clip. Methods and devices may be used in open heart surgical procedures, minimally invasive procedures and/or procedures on beating hearts or stopped hearts. Furthermore, a heart valve may be accessed by any suitable route, such as any veinous access route, through any incision(s) in the heart wall and/or atrial septum, through any heart chamber and/or through the aorta.

In one aspect of the invention, a method for constricting a valve annulus comprises introducing a plurality of clips to a heart valve annulus, the clips being coupled with a tether, securing individual clips at circumferentially spaced-apart locations about at least a portion of the annulus, and cinching the tether to circumferentially tighten the annulus. At least a first clip at a lead end of the tether is usually fixed to the tether, and the remaining clips are usually slidably coupled to the tether to facilitate cinching. Often, all of a series of intermediate clips and at least a single terminal clip will be introduced to the annulus prior to cinching by applying tension to the free end of the tether. After the proper amount of tension is applied, the terminal clip(s) will then be crimped onto or otherwise fixed to the tether to maintain the desired degree of annular constriction. Of course, it may be desirable to crimp or otherwise fix two or more clips at the lead end of the tether and/or two or more clips at the terminal end of the tether to help assure that the tether will not loosen. In some instances, it may even be desirable to deform or otherwise fix each and every clip to the tether after the desired level of cinching has been achieved. In general, however, the methods of the present invention will not rely on cinching a clip immediately after that clip is placed in order to placate tissue between adjacent clips. Deforming the portion of the at least one clip may involve applying force to at least one eyelet on the clip to reduce the inner diameter of the eyelet and secure the tether within the eyelet. Some embodiments may involve deforming two eyelets on a clip to secure the tether within each of the two eyelets.

In some embodiments, introducing the plurality of clips comprises advancing a tethered clip applicator through an incision in a wall of the heart to a desired location for treating the heart valve annulus. For example, the applicator will be introduced through an incision in the left atrial wall of the heart in some embodiments, to a location at or near the posterior or anterior commisure of the mitral valve annulus. Some embodiments further include placing an instrument introduction device through the incision in the wall of the heart, and the clip applicator is advanced through the instrument introduction device. Optionally, such embodiments may also include securing the introduction device to the heart wall before the advancing step. In some embodiments, the instrument introduction device comprises a valve, a diaphragm and/or a hemostatic barrier for allowing passage of the clip applicator and any other devices while preventing outflow of blood from the heart. In one embodiment, for example the clip applicator is generally an elongate hand-held applicator, insertable through the introduction device.

In some embodiments, securing the individual clips comprises securing a first tethered clip to the heart valve annulus and securing a plurality of subsequent tethered clips at circumferentially spaced-apart locations about at least a portion of the annulus. In some cases, the first clip is pre-secured the tether. In other cases, securing the first tethered clip to the valve annulus includes deforming a portion of the first tethered clip to secure it to the tether. Alternatively, a portion of the first tethered clip may be deformed after securing the clip to the annulus to secure the first clip to the tether. In still other embodiments, a portion of the first tethered clip may be deformed before securing the clip to the annulus to secure the first clip to the tether. In some embodiments, the plurality of subsequent tethered clips are slidably coupled with the tether. Optionally, such embodiments may further include deforming a portion of at least a second clip to secure the second clip to the tether.

In some embodiments, cinching generally involves applying tensile force to the tether. A method may further include deforming a portion of at least one of the plurality of subsequent tethered clips after the cinching step to secure the at least one partially-deformed clip to the tether. For example, deforming a portion of the at least one clip may involve deforming a last clip of the subsequent tethered clips. Optionally, such embodiments may further include deforming at least a penultimate clip of the subsequent tethered clips.

Some embodiments also include securing a tether anchor, coupled to the tether, to the valve annulus adjacent a last clip of the individual clips. For example, securing the tether anchor may involve securing a rivet to the valve annulus. Such embodiments may also include deforming a portion of the last clip around the rivet to secure the tether to the rivet and secure the last clip to the annulus. Optionally, a portion of a penultimate clip may also be deformed around the rivet to secure the tether to the rivet and secure the penultimate clip to the annulus.

Some embodiments of the method further involve visualizing the heart valve using at least one visualization device. For example any one of (or combination of) an ultrasound device, an angioscopic device, a transesophageal echocardiogram device and a fluoroscopic device may be used for visualization. In some embodiments, an ultrasound device comprising a gel-containing cone for enhancing ultrasound visualization may be used. Some embodiments may involve using a real-time Doppler ultrasound device to visualize a regurgitant flow across the heart valve during at least the cinching step. Optionally, such methods may also include visualizing a reduction in the regurgitant flow during the cinching step and selecting an amount of cinching based on the reduction in the regurgitant flow in real time. Particularly useful visualization may be accomplished using optical viewing elements disposed directly in the heart chamber, typically adjacent to the valve annulus or other target tissue being treated. Particularly in beating heart procedures, such optical visualization will be accomplished using a transparent element to exclude blood, such as a lens, a solid optically transparent block, or most preferably a transparent inflatable balloon which may be inflated with a transparent inflation medium. By engaging such balloon against the surface to be visualized, direct and highly accurate visualization of the annulus may be accomplished. In some embodiments, the optical or other visualization device is coupled with a device for introducing and securing the clips, such as the clip applicator.

As mentioned above, the introducing, securing and cinching steps may be performed as part of any suitable procedure, from any suitable access route, and the like. For example, the may be performed as part of an open heart surgical procedure, with or without stopping the heart, through one or more minimally invasive incisions and/or intravascularly. Furthermore, any suitable cardiovascular valve may be treated, such as the mitral valve, tricuspid valve or the like.

In another aspect, a method for inhibiting heart valve regurgitation comprises: introducing a plurality of crimping clips to a heart valve annulus; securing individual crimping clips at circumferentially spaced-apart locations about at least a portion of the annulus; and crimping at least one of the clips to circumferentially tighten the annulus. Crimping clips may generally be tethered or untethered, but in one embodiment the crimping clips are slidably coupled with a tether, and the method further includes cinching the tether to circumferentially tighten the annulus. Cinching typically involves applying tensile force to the tether. In some embodiments, crimping a tethered clip secures the crimped clip to the annulus and to the tether. In some embodiments, for example, crimping a clip comprises compressing at least one eyelet in the clip, the tether running through the eyelet. In some embodiments, the clips each have two eyelets and the tether runs through the two eyelets on each clip.

In some embodiments, crimping comprises crimping a first clip before the cinching step to secure the first clip to the annulus and the tether and crimping at least a last clip after the cinching step to secure the last clip to the annulus and the tether. Various embodiments may further include crimping at least a penultimate clip to secure the penultimate clip to the annulus and the tether. Crimping may further involve crimping at least the last clip around a tether anchor to secure the last clip to the tether anchor and secure the tether anchor to the annulus.

In many embodiments, at least the introducing and securing steps are performed using an elongate, hand-held, surgical device. The surgical device may include an actuator at or near its proximal end for performing at least the securing step. In some embodiments, for example, the actuator may include, but is not limited to, a trigger, a handle, a plunger, a squeeze-activated device and a syringe-grip device.

In yet another aspect, a method for inhibiting heart valve regurgitation comprises securing a flexible cord about at least a portion of the annulus of the valve and cinching the flexible cord to reduce the annular circumference. As with the above procedures, such a method may be performed as part of an open heart surgical procedure, with or without stopping the heart, through one or more minimally invasive incisions, intravascularly, or via any other suitable approach.

In some embodiments, securing and cinching are performed through a small incision in a wall of the heart. Such embodiments may further include placing an instrument introduction device in the heart wall through the incision before performing the securing and cinching steps. This method may further include securing the instrument introduction device to the wall. The instrument introduction device may include, for example, a valve for allowing passage of one or more surgical instruments while preventing outflow of blood from the heart through the valve. The method may optionally further include introducing at least one surgical instrument into a chamber of the heart through the instrument introduction device. For example, at least one elongate, hand-held instrument may be introduced for performing the securing and cinching steps.

As described above, in any of the above methods, one or more visualization devices may be used, such as ultrasound and/or transesophageal echocardiogram devices. Also as mentioned above, the methods may be used to operate on any suitable cardiovascular valves, such as a mitral, tricuspid, aortic or pulmonary valve.

In still further embodiments of the methods of the present invention, a heart valve annulus of a beating heart is constricted by first stabilizing the heart valve annulus. After the annulus is stabilized, individual clips are secured at circumferentially spaced-apart locations about at least a portion of the annulus. A tether passed through the clips may be cinched in order to circumferentially tighten the annulus. Stabilization of the beating heart is very beneficial in both minimally invasive and intravascular (closed-chest) procedures.

The valve annulus may be stabilized in a variety of ways. Usually, stabilization will involve engaging the annulus with at least a first stabilizing ring which is typically in the case of a mitral valve disposed beneath the valve leaflets to engage an intersection between the leaflets and the interior ventricular wall. Usually, the stabilization ring will be introduced from the left atrium, together with the other interventional tool(s), to a location at the valve commisure. A curved or C-shaped component of the stabilizer will then be deployed beneath the valve annulus. Preferably, a second stabilization ring will be introduced to a location above the valve annulus, where the first and second stabilizing rings will typically have similar or congruent geometries permitting clamping of the valve annulus therebetween. Optionally, either or both of the stabilizing rings may be further provided with a vacuum source, microhooks, adhesives, or the like to assist in engaging and capturing the tissue of and surrounding the valve annulus. Still further optionally, the stabilization ring disposed above the valve annulus may be adapted to deliver clips directly to the tissue, thus in some cases eliminating the need for a separate clip applier as described elsewhere in this application. Alternatively, of course, the clips may be successively applied from an applicator, as described elsewhere herein, which is advanced around at least a portion of the valve annulus while the valve annulus remains stabilized. When using a separate clip applicator, the stabilizing ring or other stabilization apparatus may provide a template to guide the applicator around the annulus as clips are applied. In most cases, the stabilization device will also shape the annulus to a geometry compatible with the applicator. After the clips are delivered, the rings or other stabilizing device will be removed, and the tether cinched to constrict the annulus as described elsewhere herein.

In yet another aspect of the method of the present invention, valve annulus may be constricted in a beating heart while directly viewing at least a portion of the valve annulus from within the atrium (left atrium in the case of the mitral valve). Individual clips are secured at circumferentially spaced-apart locations about at least a portion of the valve annulus while annulus remains under direct viewing. After the clips are properly placed, as confirmed by direct viewing, the tether may be cinched through the clips to circumferentially tighten the annulus, as generally described elsewhere in the application. Such direct viewing may be accomplished using an ultrasonic imaging element, for example one placed on a clip applier. More preferably, however, direct viewing may be accomplished by engaging a transparent element against the valve annulus and optically viewing the annulus through said element. Usually, the transparent element comprises an inflatable balloon which is inflated with a transparent inflation medium. Optical viewing may then be performed from within the inflated balloon using a fiberoptic scope, a CCD (charged coupled device), other type of camera, or the like.

In yet another aspect, a device for applying tethered clips to a heart valve annulus comprises a shaft having a proximal end and a distal end and a plurality of clips slidably coupled to a tether. The tethered clips are carried by the shaft; and the device further includes a clip applier at or near the distal end of the shaft for securing the clips to the annulus and at least one actuator at or near the proximal end of the shaft for causing the device to advance the clips and for activating the clip applier to secure the clips to the annulus. Optionally, the means for selectively advancing and securing the clips may further comprise a pusher coupled with the actuator for advancing the clips and at least one slot in an inner surface of the shaft for guiding the clips.

In some embodiments, the clip applier comprises a clip crimping member. Also in some embodiments, the at least one actuator includes means for tensioning and cinching the tethered clips to reduce the circumference of the valve annulus. The actuator itself may comprise any suitable device(s), such as but not limited to a trigger, a handle, a plunger, a squeeze-activated device, a syringe-grip device and/or any suitable foot-operated device.

In some embodiments, each of the plurality of clips includes at least one eyelet, and the tether passes through the eyelet of each clip. Optionally, in some embodiments, each clip includes two eyelets, and the tether passes through both eyelets of each clip. In such embodiments, the device may further include means for crimping the at least one eyelet of any of the plurality of clips such that a clip with a crimped eyelet is secured to the tether.

In some embodiments, the shaft comprises an elongate, hand-held shaft. Optionally, the shaft may be introducible into a patient through a minimally invasive incision. In these or other embodiments, a tether anchor may be coupled to the tether and carried by the shaft. For example, the tether anchor may comprise a rivet. The tether anchor may be coupled with at least a last clip of the tethered clips such that crimping the last clip secures the last clip to the tether anchor and the tether anchor to the tether. In some embodiments, the tether anchor is further coupled with a penultimate clip, such that crimping the penultimate clip secures the penultimate clip to the tether anchor and the tether anchor to the tether.

The tether itself may comprise any material or configuration. In some embodiments, for example, the tether comprises at least one of a suture material, a Teflon strip, a band, a filament, a wire and a strap. Embodiments including tethers may optionally also include means for cinching the tethered clips to reduce the circumference of the valve annulus.

In another aspect, a device for applying tethered clips to a heart valve annulus comprises: a shaft having a proximal end and a distal end, a plurality of clips slidably coupled to a tether, the tethered clips carried by the shaft; a clip applier at the distal end of the shaft for securing the clips to the valve annulus; and tensioning means for providing tension to the tether to cinch the tether, thus reducing a diameter of the valve annulus. In some embodiments, the clip applier comprises means for partially deforming at least one of the clips to secure the deformed clip(s) to the tether. In some embodiments, the tensioning means allows for tensioning of the tether while the clips are being secured to the valve annulus. Optionally, the device may further include cutting means at the distal end of the shaft for cutting an end of the tether after the clips have been secured and cinched.

In still another aspect or the invention, a device for treating heart valve regurgitation includes: a shaft having a proximal end and a distal end; a rotatory cord applicator at a location near the distal end, for securing a cord to the annulus of the valve; and means for cinching the cord to reduce the circumference of the valve. The shaft, for example, may comprise an elongate, handheld shaft. In some embodiments, the means for selectively advancing and securing the clips comprises a cable member coupled with the shaft. The cord may comprise any of a number of suitable materials or combinations of materials, including but not limited to a length of suture material, a length of Teflon strip, a wire, a band, and/or the like.

In another aspect, a device for applying crimping clips to a heart valve annulus comprises: an elongate, handheld shaft having a proximal end and a distal end; a plurality of crimping clips carried by the shaft; and means for selectively advancing individual clips, securing the individual clips to the annulus, and crimping each individual clip to tighten at least a portion of the valve annulus. In some embodiments, the means for selectively advancing and securing the clips comprises a cable member coupled with the shaft. As mentioned above, these crimping clips may be either tethered or untethered. Thus, some embodiments further include a tether for connecting the plurality of clips for circumferentially tightening at least a portion of the valve annulus.

In embodiments including a tether, the at least one actuator may include means for cinching the tethered clips to reduce the circumference of the valve annulus. In some embodiments, each of the plurality of crimping clips includes at least one eyelet, and the tether passes through the at least one eyelet of each clip. In some embodiments, each clip includes two eyelets, and the tether passes through both eyelets of each clip. In some embodiments, crimping the at least one eyelet of any of the plurality of clips such that a clip with a crimped eyelet is secured to the tether. More generally, any of the various features described above may be suitably used with tethered or untethered crimping clips in various embodiments.

The present invention still further provides devices for applying tethered clips to an annulus, where the device includes a shaft, a tether, a plurality of clips, and a clip applier at or near a distal end of the shaft. In particular, the tether will have at least two parallel segments, where the segments may be separate or may be simply two ends of a tether which has been folded over itself. The clips slidably receive both segments of the tether, where the clips are arranged successively on the tether. The clip applier is adapted to secure the clips individually and usually successively to the annulus while the clips remain on the tether. The use of the tether having at least one additional segment is beneficial since it provides a redundancy, i.e., if either of the segments is severed or compromised, the other remains. Moreover, in the specific embodiments, each of the clips includes at least one eyelet for receiving the tethers, preferably including two eyelets so that each segment is received in a separate eyelet. The portion of the clips surrounding the eyelets will preferably be deformable to provide for crimping of both eyelets around both tether segments, again providing for redundancy.

Apparatus according to the present invention still further includes an annular fastener. The annular fastener comprises a tether and a plurality of clips on the tether. The tether includes at least a pair of parallel segments, generally as described above, and the clips include a pair of spaced-apart eyelets, where one tether segment is received in each of the eyelets on each clip. Usually, a terminal clip will be provided on the fastener, where the terminal clip is fixed to a leading end of the tether, and may or may not include two eyelets. Usually, there will be at least two clips on the tether, more usually at least ten clips, often at least 15 clips, and sometimes as many as 30 or more. Additionally, at least a portion of the clips will be deformable in the region to permit crimping.

The present invention also provides systems comprising any of the clip delivery devices described herein. In a first instance, the system comprises a clip applier device in combination with a stabilization device which is adapted to capture and immobilize the target valve or other annulus. Typically, the stabilization device comprises a pair of rings which are adapted to clamp opposed faces of the annulus. More typically, the clamps will be adapted to clamp over and under a heart valve annulus.

Alternatively, systems according to the present invention may comprise any of the clip delivery devices in combination with a visualization device adapted to directly view a valve annulus in a heart chamber. The visualization device may comprise an ultrasonic imaging transducer, but will more typically comprise an optical viewing element disposed in a transparent element. Usually, the optical viewing element is a fiberoptic scope or a CCD, and the transparent viewing element comprises a transparent balloon inflatable with a transparent inflation medium.

BRIEF DESCRIPTION OF THE DRAWINGS

FIG. 1 is a side view of the left side of an upper body of a patient, showing an incision and a device for mitral valve repair in accordance with an embodiment of the invention.

FIG. 2A is a cut-away view of a heart, viewed from the base of the heart, with the atria cut away to view the valves, and a device for mitral valve repair in accordance with an embodiment of the invention.

FIG. 2B is a perspective view of a distal end of a device for mitral valve repair in accordance with an embodiment of the present invention.

FIG. 2C is a perspective view of multiple tethered clips according to an embodiment of the present invention.

FIGS. 25 and 26 illustrate a surgical device employing the clip advance and deployment mechanism of FIGS. 11-24 together with a tether tensioning mechanism.

DETAILED DESCRIPTION OF THE INVENTION

Figure 3A:
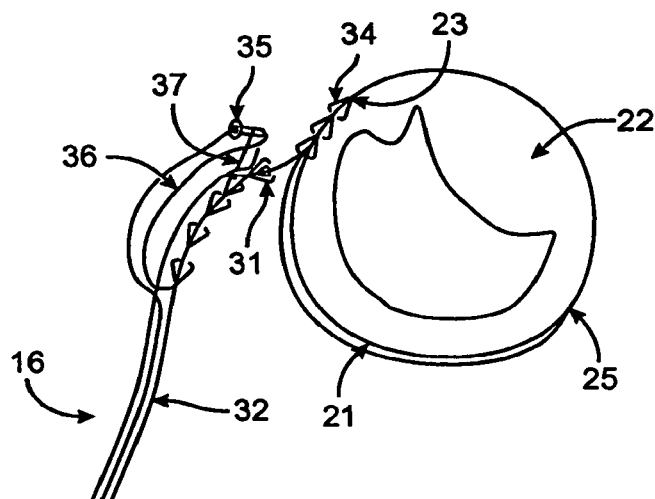
FIG. 3A is a top view of a mitral valve, with several clips placed in the mitral valve annulus, and a device for mitral valve repair in accordance with an embodiment of the invention.

Generally, the present invention provides methods and devices for repairing a heart valve, such as the mitral valve, to treat heart valve regurgitation or insufficiency. Although the following description focuses on the treatment of mitral valves, various embodiments may be used to treat other cardiovascular valves, such as tricuspid, aortic and/or pulmonary valves. Furthermore, various embodiments of devices and methods of the invention may be used in open heart surgical procedures, minimally invasive surgical procedures, or both. Although minimally invasive valve repair may be advantageous in some circumstances, in other cases it may be advantageous to perform an open procedure. If the heart is to be stopped, for example, it may be advantageous to perform an open procedure to reduce the amount of time the patient is placed on cardiopulmonary bypass. The devices and methods of the invention themselves may also reduce the overall duration of a valve repair procedure, thus reducing the time the patient is on cardiopulmonary bypass.

Generally, devices and methods of the invention involve coupling one or more devices with a valve annulus and using the devices to reduce the circumference of the annulus to reduce valve regurgitation. In some embodiments, methods involve securing a flexible cord about at least a portion of the annulus of the valve and cinching the flexible cord to reduce the annular circumference. Some embodiments, for example, involve placing multiple tethered anchoring devices into the mitral valve annulus. The tether is then tightened, applying force to the anchoring devices, to reduce the circumference of the mitral valve annulus. In some embodiments, clips may be crimped to reduce the annular circumference. Such crimping clips may be used with or without a tether in various embodiments. In other embodiments, a tethering device such as a rotatory cord may be applied to a valve annulus to tighten the annulus. Other embodiments may involve one or more other suitable techniques. Therefore, the following description is provided for descriptive purposes only and should not be interpreted to limit the scope of the invention as set forth in the claims.

Referring now to FIG. 1, a patient 10 undergoing valve repair according to various embodiments of the invention may require neither cardiopulmonary bypass nor a large skin incision. In other embodiments, an open heart surgical procedure, cardiopulmonary bypass or both may be employed. In some embodiments, an endotracheal tube may be used to ventilate patient 10 (not shown) while allowing the patient's left lung to collapse to allow better access to the heart. A small incision 14 may be made in the left thorax of the patient, to admit a mitral valve repair device 16. In one embodiment, for example, an incision of between about 0.5 and about 5 inches, and preferably between about 1 and about 3 inches, may be made in the fifth intercostal space of patient 10. Any other minimally invasive incisions may alternatively be used in various embodiments. In other embodiments, any suitable open heart surgical incisions and procedures may be used, either on a beating heart or on a stopped heart using cardiopulmonary bypass. Alternatively, some devices and methods may be used intravascularly.

At any suitable time before or during a mitral valve repair procedure, an imaging device may be placed in or on the patient to monitor the progress of the procedure. For example, in some embodiments a 3-dimensional, transesophageal echocardiogram device and/or a fluoroscopic C-arm may be used for visualization. After a skin incision is made, one or more various devices may then be used to navigate a path between the skin incision and the patient's heart. For example, an imaging devices such as an angioscope, as well as cutting and/or suturing devices may be used. Cutting and/or suturing devices may then be used to make a small incision in the left atrium, for example at the left atrial appendage. In one embodiment, an incision and a purse string suture will be used to gain access to the left atrium. Any suitable access methods or devices may be used, however, to gain surgical access to the mitral valve (or other valve to be repaired). As noted briefly above, methods of the present invention may typically be performed on a beating heart, thus eliminating the need for cardiopulmonary bypass. It is contemplated, however, that many embodiments will also be suitable for use in open-heart surgery techniques and/or in conjunction with use of cardiopulmonary bypass.

In some embodiments, repair device 16 will then be advanced into the left atrium through the incision, purse string suture, or other access site. In other embodiments, as described further below, an instrument introduction device may be inserted into the incision in the heart wall and may be secured to the wall, such as with suture material. At or near the distal end of repair device 16, one or more repair actuators (not shown in FIG. 1) will be used to repair the mitral valve. For example, in various embodiments, repair actuators may include a device for applying a cord to a valve annulus, such as a rotatory device for applying a cord such as a suture or Teflon strip. A repair actuator may also include a suture cutter, a suture tightening device, a clip application device, a fastener application device, an imaging device, or any other suitable device or combination thereof.

In many embodiments, the repair actuators will be generally configured to attach one or more fasteners to the mitral valve annulus and to tighten the fasteners to cinch, or tighten, the mitral valve annulus, thus decreasing the overall circumference of the mitral valve and reducing mitral regurgitation. In other embodiments, however, a fastener or other device may be placed across the valve, a device may be placed to bolster or increase the bulk of the valve annulus, or the like. Therefore, the invention is in no way limited to including fasteners, sutures, or the like.

Referring now to FIG. 2A, repair device 16 is shown in relation to a cross-section of a heart 20. Heart 20 is viewed from the perspective of the base of the heart (roughly, the top or cephalic part of the heart), as if the right and left atria were removed. The pulmonary 26, aortic 28, tricuspid 24 and mitral 22 valves are shown, as well as the mitral valve annulus 21 and the anterior commisure 23 and posterior commisure 25 of mitral valve 22.

Repair device 16 suitably includes an elongate shaft 32, a proximal actuator 27, and several distal repair actuators. In one embodiment, as shown more clearly in FIG. 2B, repair actuators include a clip applicator 31, a series of clips 34 connected by a tether 36, a rivet 35 also connected to tether 36, and a rivet holder 37. As already discussed, repair device 16 may include more, fewer, or different distal repair actuators in various embodiments, without departing from the scope of the invention. Further discussion of the distal features of one embodiment of repair device 16 are discussed further below in relation to FIGS. 11-25. Furthermore, any parts of repair device or devices to be used in mitral valve repair may be made radiopaque to facilitate imaging.

As shown in FIG. 2B, elongate shaft 32 may include a bent or otherwise shaped portion near its distal end. Repair device 16 may also comprise any suitable means for applying clips 34, such as clip applicator 31 in the form of an adjustable jaw. In some embodiments, elongate shaft 32 includes a lumen for containing clips 34, tether 36 and/or other elements for applying or cinching clips 34 or the like.

Referring now to FIG. 2C, repair device 16 may generally be configured to hold a plurality of clips 34, for example within shaft 32. In some embodiments, for example, clips 34 may be housed in a cartridge-like configuration which may fit within elongate shaft 32. Clips 34 may be made of any suitable material, such as Nitinol™ (NiTi), stainless steel, titanium, or the like. Additionally, clips 34 may have any suitable configuration and size for attaching to a portion of the mitral valve such as the mitral valve annulus. Although V-shaped, hinged clips 36 with prongs are shown, U-shaped clips, T-shaped clips, multiply-bent clips, straight clips and/or the like may be used in various embodiments. In some embodiments, at least the most distal clip 34n, typically a first clip to be placed in valve annulus 21, may be coupled with an end of tether 36. More than one clip may be coupled as well, in various embodiments. Coupling of one or more clips 34 with tether 36 may be accomplished by any suitable means. In one embodiment, for example, a radiopaque tether anchor 39 is used to anchor tether 36 to a first clip 34. In other embodiments, attachment may be made with adhesive, solder, knotting of the tether or the like. Subsequent clips 34 are then typically suspended on tether 36. The clips 34 may be attached to tether 36 of may be freely suspended thereon.

In some embodiments, clips 34 will be configured as double-clips or crimping clips. Such crimping clips, for example may be configured similarly to two V-shaped clips, connected together at the bottom of the V. Each crimping clip may be attached to valve annulus tissue at two locations, adjacent to one another, and the clip may be crimped, to squeeze, pinch, or pleat annular tissue within the clip. Thus, multiple crimping clips may be applied circumferentially to an annulus to crimp, or tighten, tissue along the annulus, thereby tightening the annulus and reducing regurgitation. In some embodiments, such crimping clips will be used without a tether, while in other embodiments they will be coupled with a tether to provide for further annulus tightening. As with clips 34 described above, such crimping clips may have any suitable size, shape and configuration and are not limited to V-shaped double clips.

Tether 36 generally runs between a first clip 34, or a device coupled with first clip 34, through each of a plurality of subsequent clips 34, to rivet 35. Tether 36 may be coupled with each clip by any suitable means. For example, in FIG. 2B tether 36 runs through a hole or eye in each clip 34. In other embodiments, tether 36 may be tied, attached with adhesive, wrapped, or otherwise attached to each clip. Generally, repair device 16 will be configured to place successive clips 34 along a mitral valve annulus 21, attaching each clip 34 to the annulus, for example by using clip applicator 31. Thus, after one clip 34 is attached, another clip 34 will be fed or will naturally fall or otherwise be positioned within clip applicator 31 for application to the valve annulus.

Tether 36, which couples clips 34 and rivet 35 together may be any suitable substance for coupling and/or tightening multiple fastening devices. For example, in some embodiments tether 36 will be conventional, durable suture material, having a diameter between about 1 mm and about 3 mm, and preferably about 2 mm. In other embodiments, a pre-shaped Teflon strip having a diameter between about 1 mm and about 6 mm, and preferably between about 2 mm and about 5 mm, may be used. Those skilled in the art will recognize that any suitable suturing, coupling, tensioning or similar devices may be used to tether and/or add tension between clips 34.

With continued reference to FIG. 2C, in some embodiments, a second tether anchor is coupled with tether 36 and clips 34 to better allow tether to be cinched. In one embodiment, second tether anchor comprises a rivet 35, or multiple rivets 35. Rivet 35 is positioned near the proximal end of clips 34, while first tether anchor 39 is positioned near the distal end. Rivet 35, for example, may include a hollow bore, through which tether 36 runs, and may be positioned to fit within one or more proximal clips 34*a-b*. In some embodiments, crimping proximal clips 34*a-b* to attach them to a valve annulus will also close the clips 34*a-b* around rivet 35 to secure rivet 35 to tether. For example, in one embodiment all clips 34 other than proximal clips 34*a-b* will be secured to a valve annulus. Tether 36 will then be cinched, by applying tensile force to tether 36 in a proximal direction (arrows). Once a desired amount of cinching force is achieved, proximal clips 34*a-b* may be crimped to secure tether 36 within rivet 35 and to secure proximal clips 34*a-b* over rivet 35 and to the valve annulus. In various embodiments, rivet 35 may be preloaded or pre-inserted into one or more proximal clips 34*a-b*. In other embodiments, rivet 35 may be moved into contact with proximal clip(s) 34*a-b*, by an advancing device or the like. In still other embodiments, any suitable rivet holder 37 may be used to hold and place rivet 35 to allow rivet 35 to act as a tether anchor. In one embodiment, for example rivet holder 37 may be a simple arm-like device. In other embodiments, rivet holder 37 may be a forceps-like device used to place and release rivet 35 at a desired location.

Generally, tether 36 may be coupled with each clip 34 or other attachment device, and with rivet 35, and one end of tether 36 then runs proximally back towards proximal actuator 27. In one embodiment, an end of tether 36 runs through shaft 32 of repair device 16 to a location at or near handle, so that a surgeon or other physician using the device may use the tether 36 to apply force or tension to clips 34, rivet 35 and the like. In other embodiments, other suitable tethering and/or tightening devices may be used.

Figure 8:
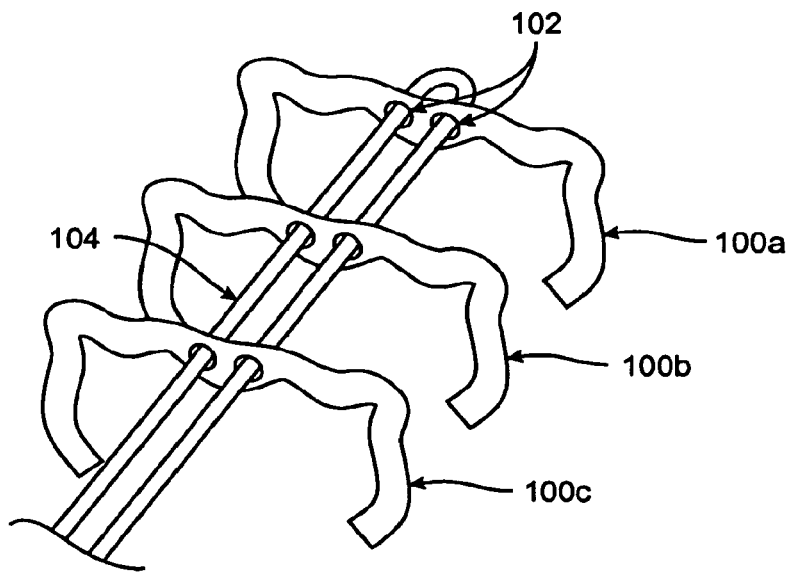
FIG. 8 is a perspective view of clips and a tether in accordance with one embodiment of the present invention.

With reference to FIG. 8, another embodiment of a clip 100 and tether 104 is shown. In some embodiments, clips 100 may include two or more eyelets 102, rather than only one eyelet. In such embodiments, tether 104 may run through both eyelets on each clip 100. In one embodiment, tether 104 runs through one eyelet 102 of each clip 100, forms a loop around the far end of the first (or most distal) clip 100*a*, and a parallel segment then runs back through the other eyelet 102 of each clip 100. In some versions, both ends of tether 104 may then be pulled proximally to cinch the tethered clips 100. In general, tethering each clip through two or more eyelets may be advantageously stronger and more durable that tethering each clip through one eyelet. In alternative embodiments, various forms of securing devices may also be used, such as a washer or dowel-like securing device around tether to run through eyelets 102 of the first clip 100*a*. Furthermore, tether 104 may be secured at or around a first clip 100*a* or other clips via any suitable means. For example, two tethers may be tied distal to the first clip 100*a* or the like.

Figure 10B:
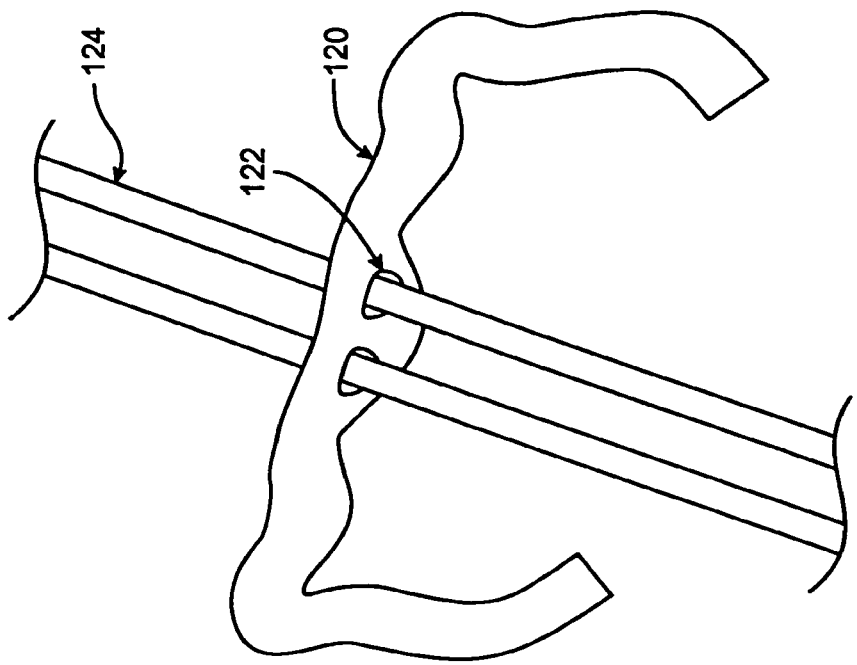
FIGS. 10A and 10B are perspective views of a crimping clip and a tether in accordance with one embodiment of the present invention.
Figure 10A:
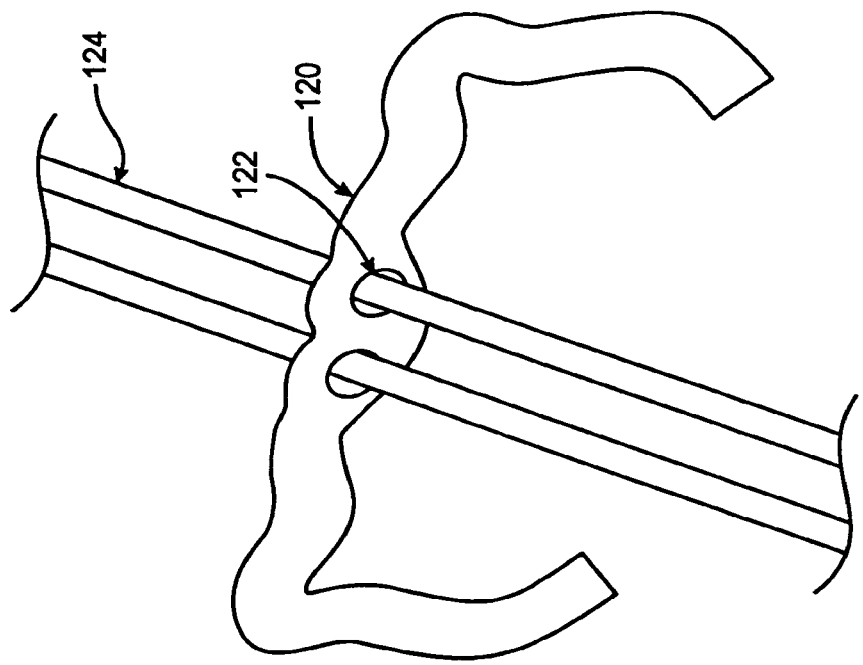

With reference now to FIGS. 10A-10B, some embodiments include one or more crimping clips 120. Crimping clips 120 may be used in some embodiments with tethers 124 and in other embodiments without tethers. In some embodiments, for example, a tether 124 may run through two eyelets 122 on each crimping clip 120. In an uncrimped clip 120, as shown in FIG. 10A, tether 124 passes relatively freely through eyelets 122. Thus, for example, tether 124 may be pulled through eyelets 122 of the uncrimped clip 120 to cinch multiple clips to help reduce the diameter of the valve annulus. When desired, such as after cinching, clip 120 can be crimped, as shown in FIG. 10B. Crimping clip 120 involves deflecting eyelets 122 is some way so as to reduce their inner diameter. In some embodiments, for example, a surgical device for placing crimping clips 120 includes a pusher, bar or other device for pressing a portion of clip 120 to depress or deflect eyelets 122. When the inner diameter of eyelets 122 is reduced, the eyelets 122 will tend to trap or secure tether 124 inside the inner diameter, thus securing tether 124 in place. Thus, crimping clips 120 may be secured to a valve annulus and further secured to tether 124 via crimping. Many other suitable configurations, shapes, sizes and the like are contemplated for crimping clips other than those shown in FIGS. 10A-10B.

Referring again to FIG. 2A, proximal actuator 27 of repair device 16 generally includes any suitable device (or devices) for manipulating and actuating the distal repair actuators. Proximal actuator 27 generally allows a surgeon or other physician to manipulate repair device 16 and activate one or more of the distal features to perform a procedure. In one embodiment, proximal actuator 27 includes two or more gripper devices that act like a scissor mechanism. Alternatively, other proximal actuators 27 may include a trigger, a handle, a plunger, a squeeze-activated device, a syringe-grip device and/or any other device for moving and activating distal features/actuators of device 16. In some embodiments, proximal actuator 27 may include a tether holder, tether cinching means, a clip adjuster, attachment for an imaging device and/or the like.

Figure 9:
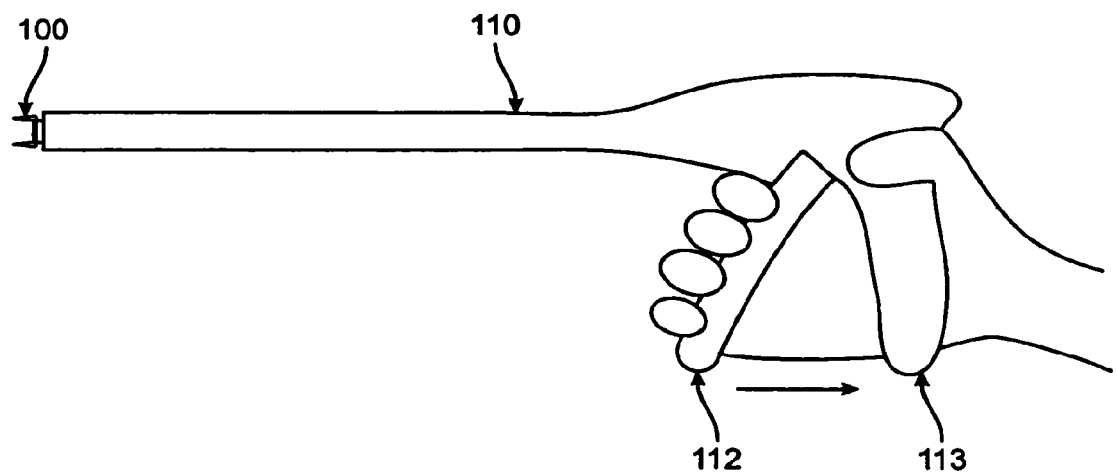
FIG. 9 is a side view of a surgical device for repairing a cardiovascular valve according to one embodiment of the present invention.

Referring to FIG. 9, for example, an alternative embodiment of a surgical device 110 is shown, having a distal end with means for applying a clip 100 and a proximal end comprising a handle 113 and a trigger 112. Trigger 112 may be moved proximally (arrow) to perform a function, such as advancing and/or applying a clip 100. Alternatively, trigger 112 and handle may be replaced by a thumb- or finger-activated plunger device, a syringe-grip type device, a squeeze-activated device, or any other device or combination. Generally, any suitable proximal actuator is contemplated.

Referring now to FIG. 3A, a repair device 16 is shown applying clips 34 to a mitral valve annulus 21. In some embodiments, a first clip 34 may be placed and attached to the valve annulus 21 at or near the anterior commisure 23 and subsequent clips may be placed and attached in a direction moving along the annulus 21 towards the posterior commisure 25. In other embodiments, it may be advantageous to start at or near the posterior commisure 25 and move towards the anterior commisure 23. In still other embodiments, clips 34 may be started at a location apart from either commisure.

Figure 3B:
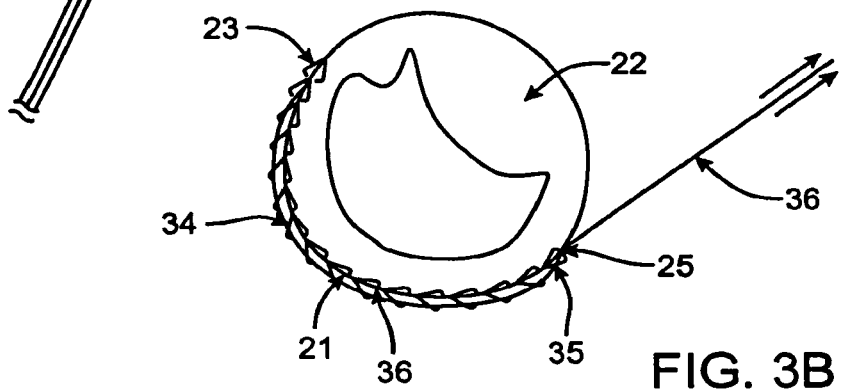
FIG. 3B is a top view of the mitral valve of FIG. 3A, with clips in place along the length of the mitral valve annulus.

FIG. 3B shows the same mitral valve with clips in place and attached to the mitral valve annulus 21 from the anterior commisure 23 to the posterior commisure 25. Furthermore, the clips 34 are coupled with tether 36 and rivet 35 is coupled to clips 34 via tether 36. One end of tether 36 is shown exiting the mitral annulus 21, clips 34, and rivet 35. Typically, this free end of tether 36 would be contained within repair device 16 and would be accessible for use in applying tensile force to tether 36 in a proximal direction (arrows). For example, as explained above, the free end of tether 36 may run through repair device to a location outside patient 10, to allow a physician to apply tension to tether 36.

Figure 3C:
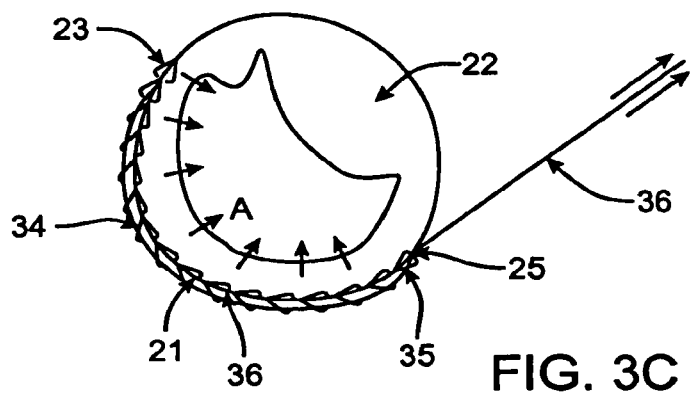
FIG. 3C is a top view of the mitral valve of FIGS. 3A-B, with clips in place along the length of the mitral valve annulus and with suture connecting and tightening the clips to reduce the circumference of the annulus.

In FIG. 3C, tether 36 has been used to apply tension (arrows) to and between clips 34 to apply force to mitral annulus 21. The force generated will generally be inwardly directed force, towards the center of the mitral valve 22, as is shown by arrows A. This force will also tend to pull clips 34 towards one another, causing the circumference of the mitral valve 22 to decrease and, thus, helping to decrease mitral regurgitation. As mentioned above, in some embodiments it is possible to crimp one or more clips 34 before applying tension to tether 36. Crimping may more securely attach a clip 34 to the annulus, may secure a clip 34 to tether 36, or both.

Figure 3D:
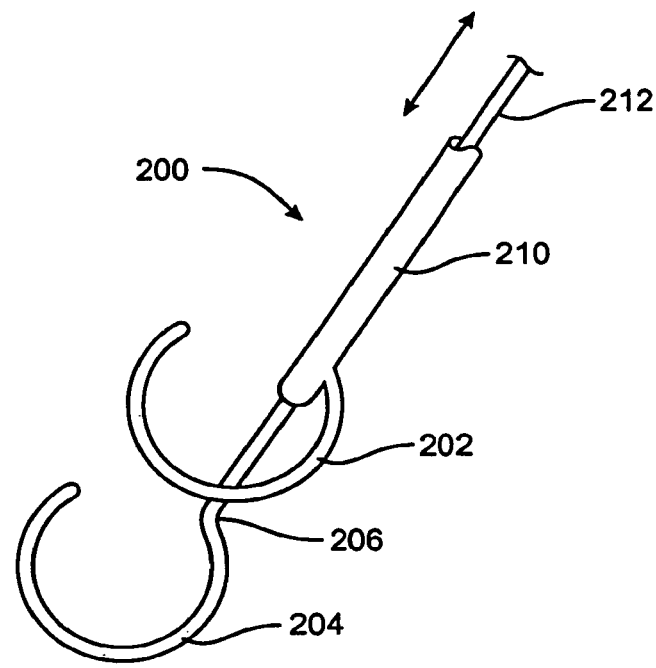
FIG. 3D is a schematic illustration of a heart valve stabilization device which may be used in the methods of the present invention.

When the methods of the present invention are performed on beating hearts, either in minimally invasive procedures through ports or otherwise as described herein, or via an intravascular (closed chest) approach, it will be desirable to be able to stabilize and/or locate the valve annulus. It is important that the clips be applied to the fibrous tissue of the annulus and in particular that they not be delivered into the leaflet tissue or the tissue of the atrial wall, neither of which will provide the desired purchase for holding the clip. An exemplary method for achieving such stabilization utilizes a clamping device, such as device 200 illustrated in FIG. 3D. Clamping device 200 includes an upper or atrial ring 202 and a lower or ventricular ring 204, typically adapted for placement above and below the annulus of the mitral valve. The rings 202 and 204 will typically be formed from an elastic material having a geometry selected to engage and optionally shape or constrict the valve annulus. For example, the rings may be formed from shape memory alloy, such as nitinol, from a spring stainless steel, or the like. In other instances, however, the rings could be formed from an inflatable or other structure can be selectively rigidized in situ, such as a gooseneck or lockable element shaft.

Figure 3E:
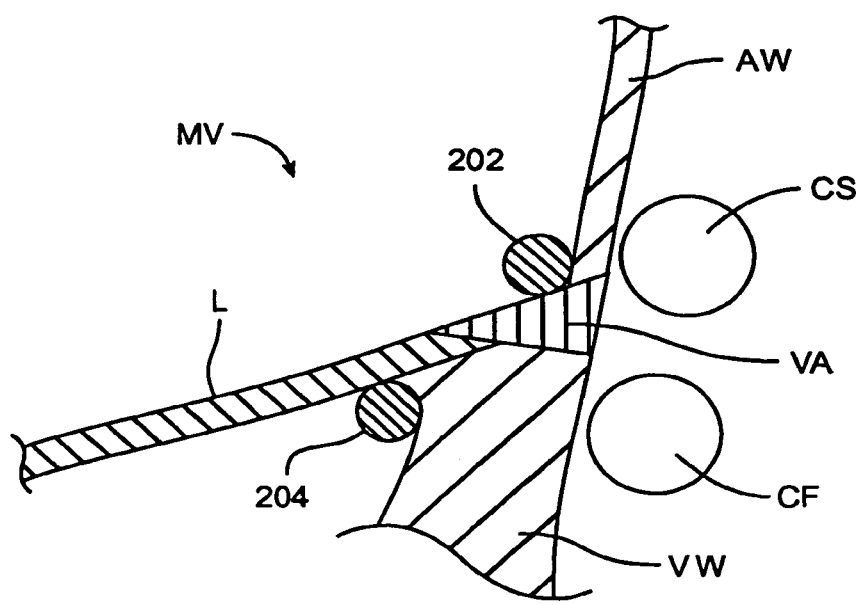
FIG. 3E is a schematic illustration showing where the atrial clamp and ventricular clamp of the stabilization of FIG. 3D will be located on a mitral valve annulus.
Figure 3F:
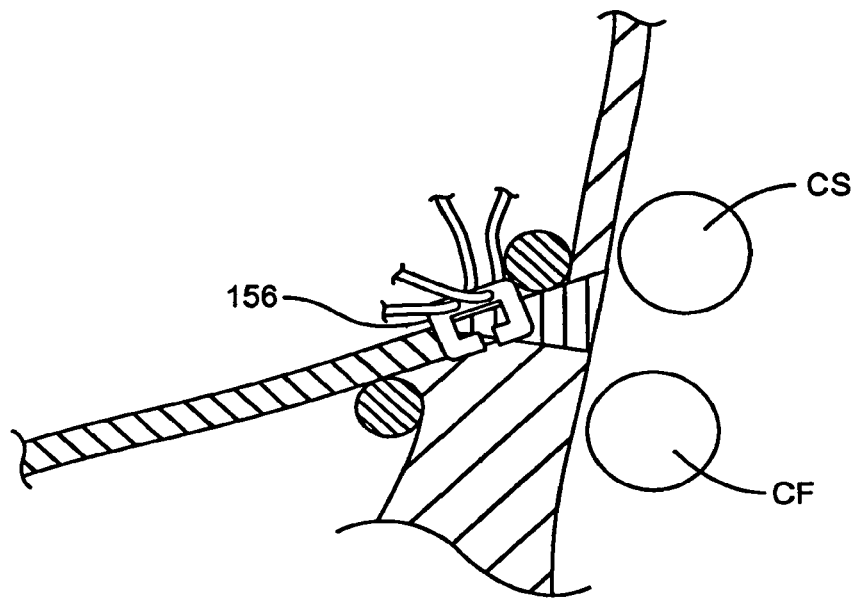
FIG. 3F illustrates an exemplary clip of the present invention which has been secured in a mitral valve annulus using the stabilization device of FIGS. 3D and 3E.
Figure 3G:
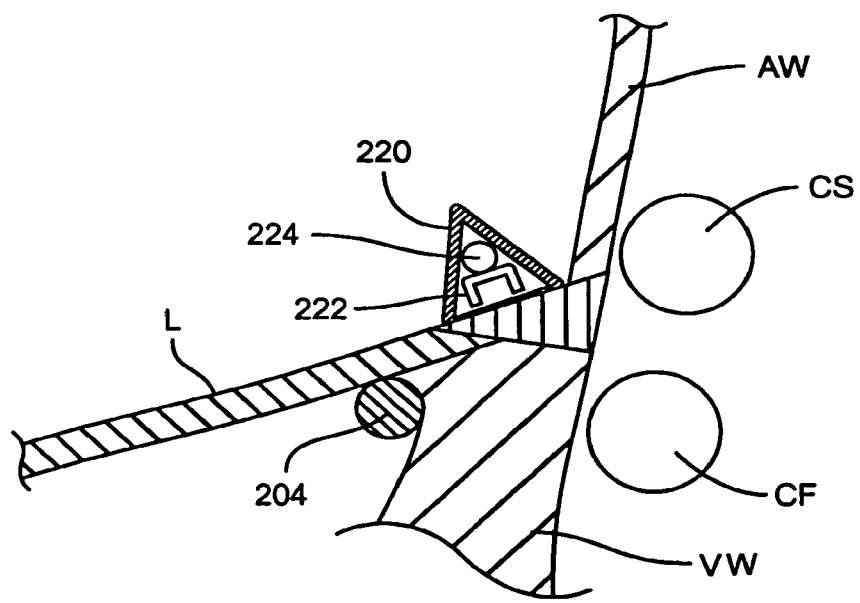
FIG. 3G illustrates an alternative construction for a stabilization device, where the atrial ring comprises a mechanism for delivering clips to the valve annulus while the valve remains stabilized with the stabilization device.

The device 200 will be introduced to the left atrium of a beating heart, either transeptally or through an incision in the heart wall, as described hereinafter in connection with the clip appliers of the present invention. Once in the atrium, the lower or ventricular ring will be introduced through the mitral valve opening, with a corner 206 of the ring typically being engaged against a commisure. The ventricular ring 204 may be adjusted so that it lies at a junction between the valve leaflet L and the ventricular wall VW, as illustrated in FIG. 3E. The upper or atrial ring 202 may then be clamped down onto the upper surface of the annulus VA, typically by sliding an outer shaft 210 down over an inner shaft 212. Thus, the annulus will be circumferentially clamped between the rings, again as observed in FIG. 3E. Such clamping will stabilize the annulus relative to the remainder of the beating heart, thus facilitating subsequent clip application. For example, the clip appliers described elsewhere herein may be used to introduce individual clips 156, as illustrated in FIG. 3F. Alternatively, the atrial stabilization ring 202 could be replaced with a circular clip applier 220, as shown in FIG. 3G. A stabilization device employing such a clip applier could be used to simultaneously stabilize the annulus and deliver clips 222 using a clip driver, such as a balloon 224.

Although not illustrated, in some instances it may be desirable to provide a third stabilization element on the exterior of the heart, optionally between the coronary sinus CS and circumflex artery CF or within the coronary sinus.

Figure 4A:
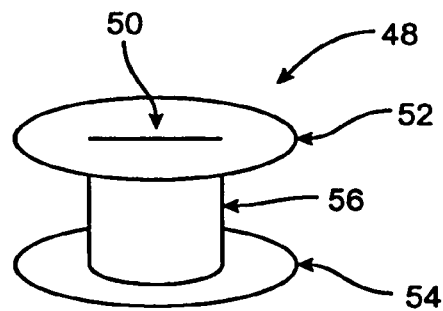
FIG. 4A is a perspective view of an instrument introduction device for introducing a device through a heart wall in accordance with an embodiment of the invention.

With reference now to FIG. 4A, some embodiments of the invention include an instrument introduction device 48 for facilitating introduction and manipulation of one or more instruments through a heart wall to perform a surgical procedure on a heart valve. In some embodiments, such a device 48 includes an outer surface 52, an inner surface 54, a hollow member 56 coupled between the surfaces and a valve 50 coupled with hollow member 56. Generally, device 48 may have any suitable size and configuration and may be made of any suitable material or combination of materials. Device 48 is typically placed through a small incision on a heart wall, such that hollow member 56 is disposed within the heart wall, outer surface 52 is disposed on the outer surface of the heart wall, and inner surface 54 is disposed on the inner surface of the heart wall. Valve 50 comprises a one-way valve which allows one or more instruments to be introduced through device 48 into a heart chamber but which prevents blood from escaping out of the heart chamber through valve 50.

Figure 4B:
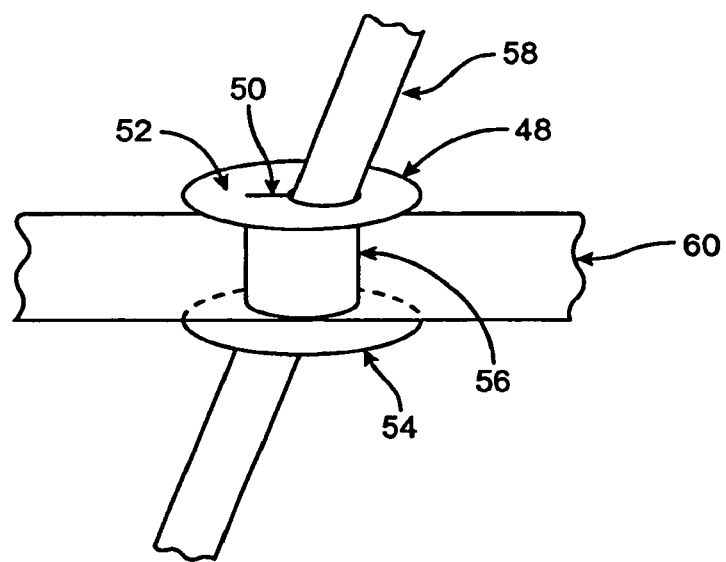
FIG. 4B is a perspective view of an instrument introduction device as in FIG. 4A in position in a section of a heart wall, with an instrument in place in accordance with an embodiment of the invention.

Referring now to FIG. 4B, instrument introduction device 48 is shown within a section of a heart wall 60 and with a surgical instrument 58 extending through valve 50 and hollow member 56. In some embodiments, device 48 may be removably attached to heart wall 60 by a surgeon, for example by a purse-string suture or other means. Generally, device 48 not only protects against blood loss during a surgical procedure but also reduces trauma to heart wall 60 from manipulation of surgical instruments 58. Thus, device 48 and its various component parts may have any configuration, size and the like for achieving such effects in a heart valve surgery and any suitable configuration is contemplated. A suitable introduction device is described in co-pending application 60/462,502, the full disclosure of which is incorporated herein by reference.

Figure 5A:
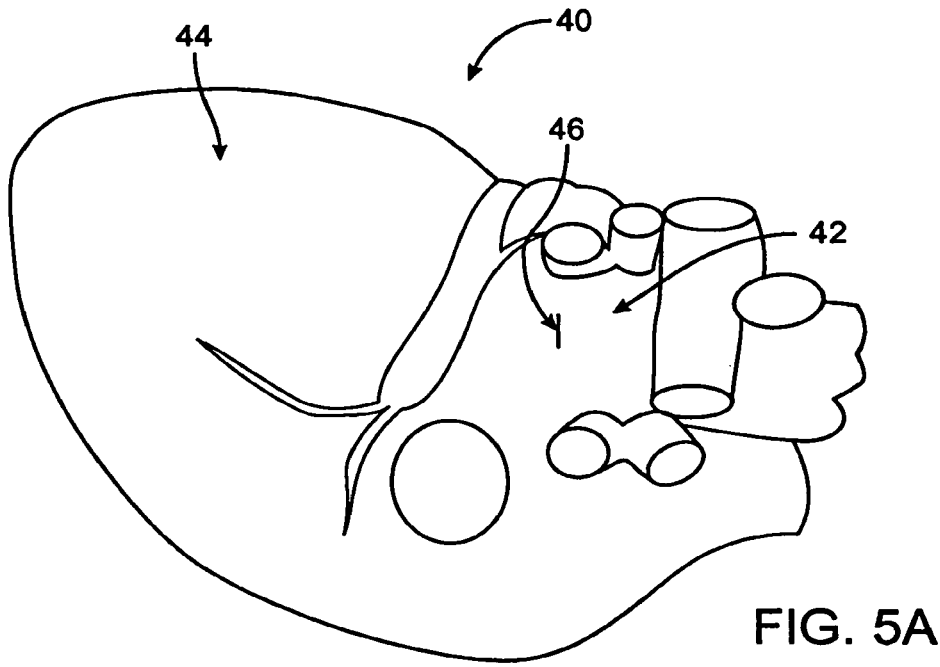
FIG. 5A is a perspective view of a heart with a small incision in the wall of the left atrium.
Figure 5B:
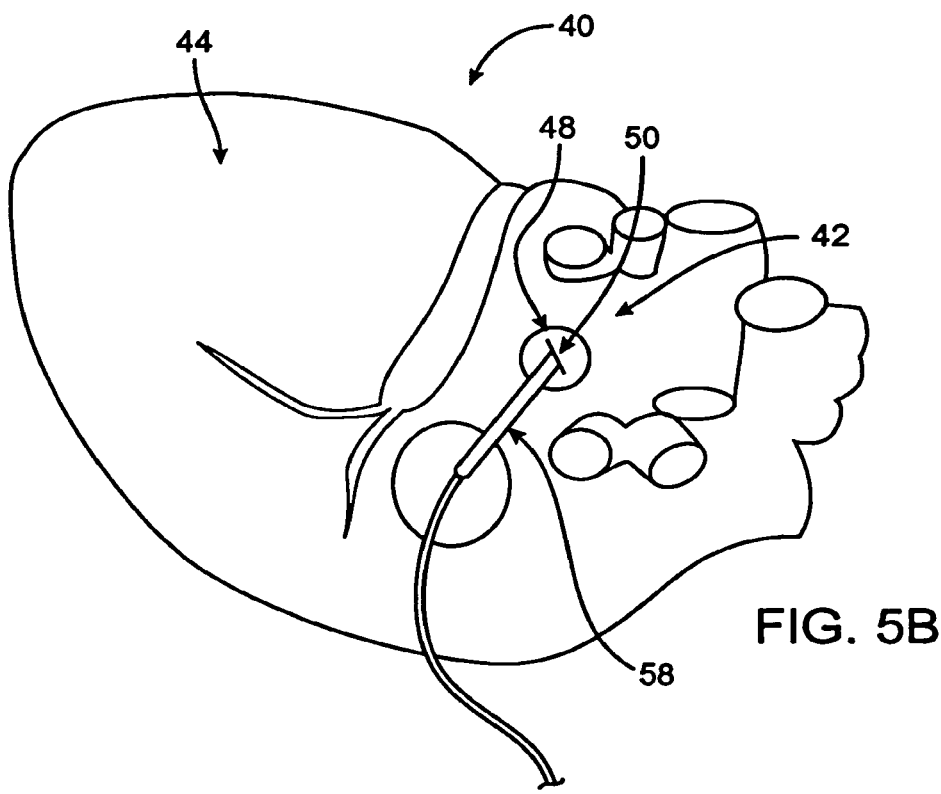
FIG. 5B is a perspective view of a heart as in FIG. 5A, with an instrument introduction device through the wall and an instrument placed through the device in accordance with one embodiment of the invention.

With reference now to FIG. 5A, a heart 40 is shown from a left, side view, showing the outer surface of the left ventricle 44 and the atrium 42. As shown, many methods of the invention may be performed via a minimally invasive incision 46 in the left atrial wall. In some embodiments, as described above and as shown in FIG. 5B, instrument introduction device 48 may be placed through the incision 46, into a position within the wall of the heart. Once device 48 is in place, one or more surgical instruments 58 may be placed through device 48 to perform a surgical procedure. In fact, multiple instruments 58 may be used one at a time, introducing each instrument through device 48 in some embodiments.

Figure 6:
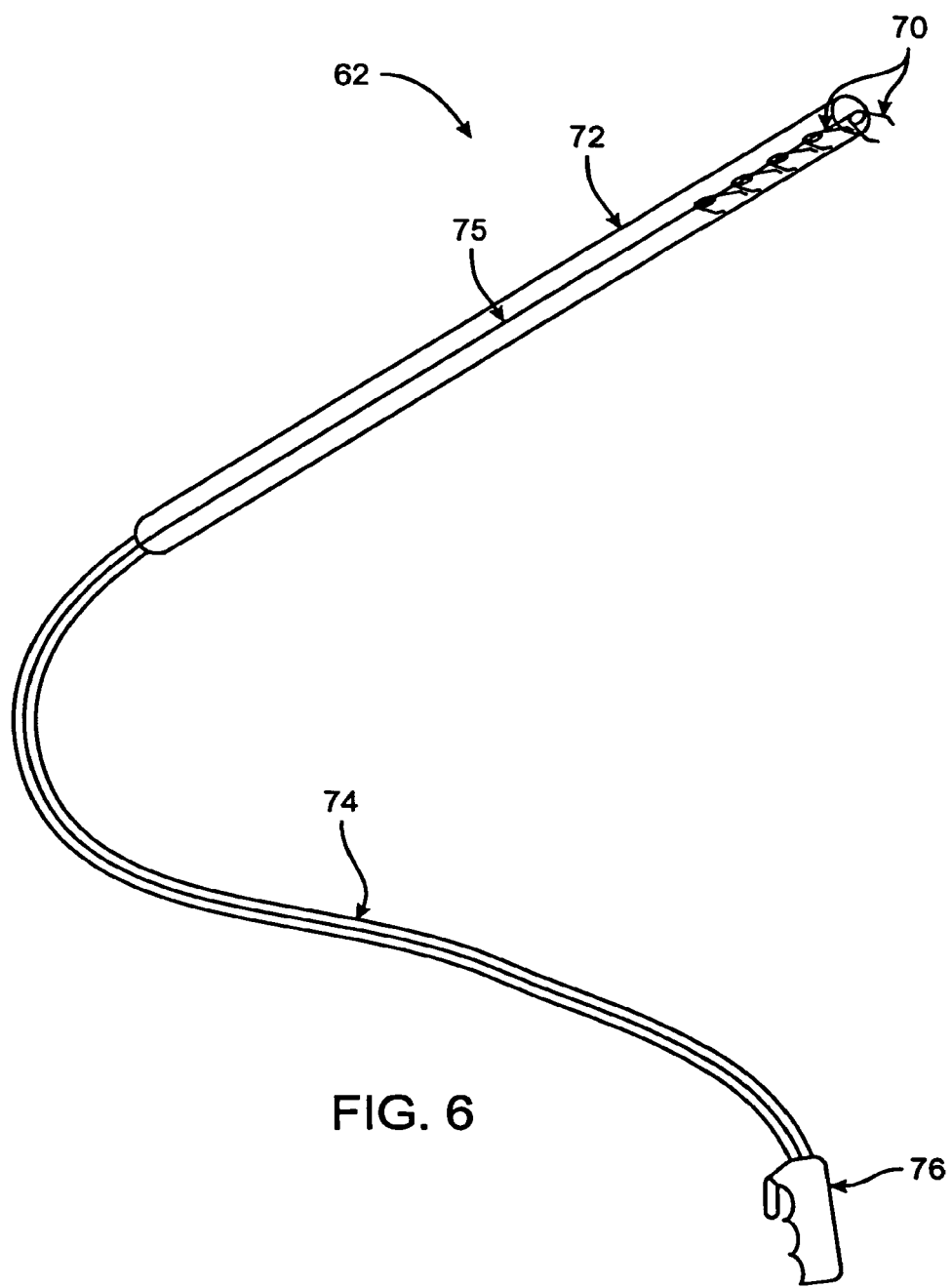
FIG. 6 is a perspective view of a device for treating a heart valve in accordance with an embodiment of the present invention.

With reference now to FIG. 6, one embodiment of a device 62 for performing minimally invasive heart valve repair suitably includes a thin, tubular, handheld shaft 72, coupled at its proximal end with a connector 74 which in turn is coupled with an actuator 76. Shaft 72 may have any suitable shape, size and configuration to allow convenient manipulation of device 62 by a surgeon to perform a surgical valve procedure. In one embodiment, for example, shaft 72 is shaped like a thin wand or pencil-like apparatus which may be held and manipulated with one hand of a surgeon and may be inserted into a chamber of the heart through a small, minimally invasive incision or introduction device. Shaft 72 will typically be used to place and secure one or more tethering clips 70 or other tethering devices in a valve annulus, such as the mitral valve annulus, and may also be used to cinch connected tethering devices to tighten the valve. In one embodiment, a cable 75 runs longitudinally through all or a part of shaft 72 and continues through connector 74 or a similar housing to actuator 76. Actuator 76 may then act through cable 75 to advance clips 70 through shaft 72 and/or to apply clips 70 to a valve annulus or other area on or around a valve. Thus, a device 62 as shown in FIG. 6 may include shaft 72 for manipulating and positioning with one hand of a surgeon and a coupled actuator 76 for use by the other hand of the surgeon or by another person, such as an assistant. A thin shaft 72 will typically be easy to manipulate and position, to enhance the accuracy and convenience valve surgery procedures.

Figure 7A:
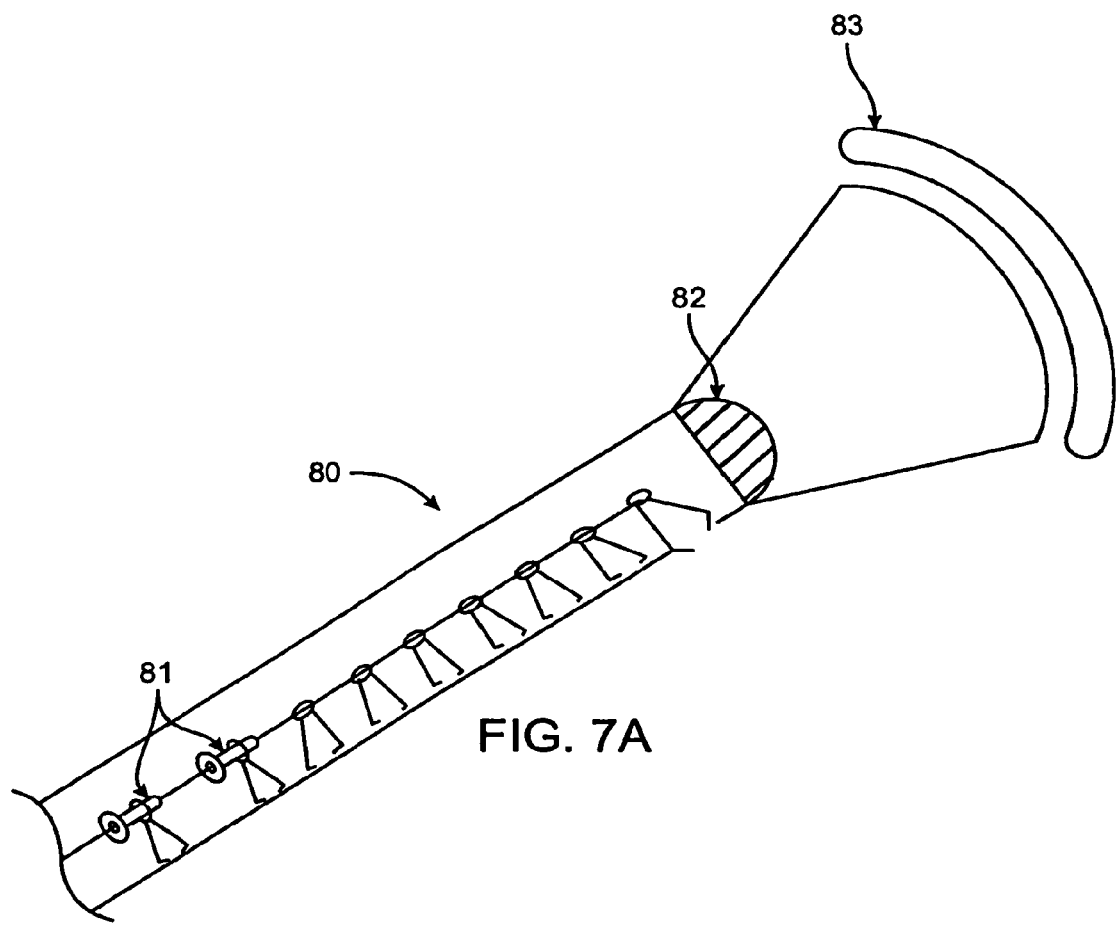
FIG. 7A is a side view of a distal end of a heart valve treatment device having an attached ultrasound transducer as in an embodiment of the present invention.

With reference now to FIG. 7A, a surgical device 80 for surgically treating a heart valve may suitably include an ultrasound transducer 82 at or near the distal end of the device for enhancing visualization of a valve annulus 83, other surgical site, surgical instruments and/or the like. For example, ultrasound transducer 82 may comprise a distal tip which may be removably or permanently attached to the distal end of surgical device 80. The embodiment in FIG. 7A also includes multiple rivets 81, which may be included to further enhance coupling of the tether and clips. In another embodiment, ultrasound transducer 82 may be coupled with device 80 near the distal end at a different location, may be permanently integrated into device 80 and/or the like. Any suitable ultrasound transducer 82 may be used.

Figure 7B:
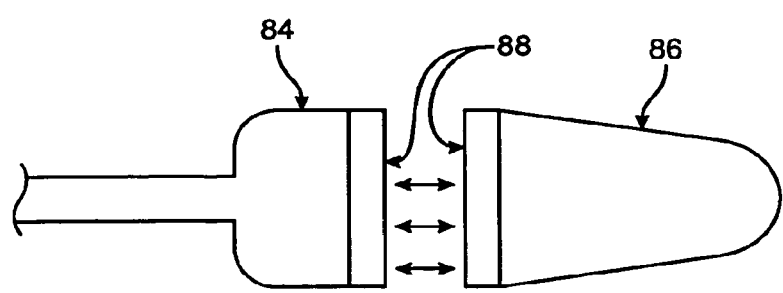
FIG. 7B is a side view of an ultrasound transducer and a gel-filled cone for enhancing ultrasound visualization in accordance with one embodiment of the present invention.

In another embodiment, and with reference now to FIG. 7B, visualization of a heart valve surgical site and heart valve procedure may be enhanced by use of a conventional ultrasound transducer 84 coupled with a gel-filled or fluid-filled cone 86. Cone 86 may have any suitable shape, size and overall configuration and may be filled, or partially filled, with any suitable gel or fluid for enhancing transmission of ultrasound signals from transducer 84. Generally, transducer 84 and cone 86 may be coupled together via complementary coupling surfaces 88 or any other suitable means. Once transducer 84 and cone 86 are coupled, cone 86 may then be used to contact a surface of a heart to begin ultrasound visualization. The gel or fluid in cone 86 allows for efficient ultrasound transmission and visualization without requiring placement of gels or fluids directly onto heart tissue. Thus, ultrasound transducer 84 may be used to effectively aid visualization of the heart without introducing unwanted gels, fluids, or the like into or onto the heart.

Figure 7C:
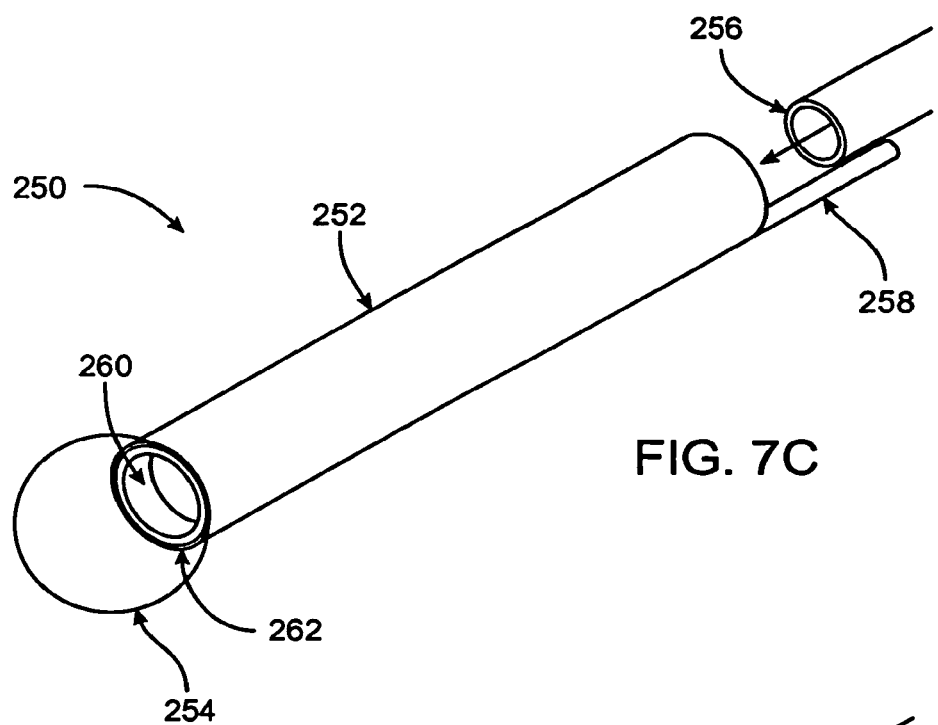
FIG. 7C illustrates an optical viewing device useful in the methods of the present invention and comprising a fiberoptic scope.
Figure 7D:
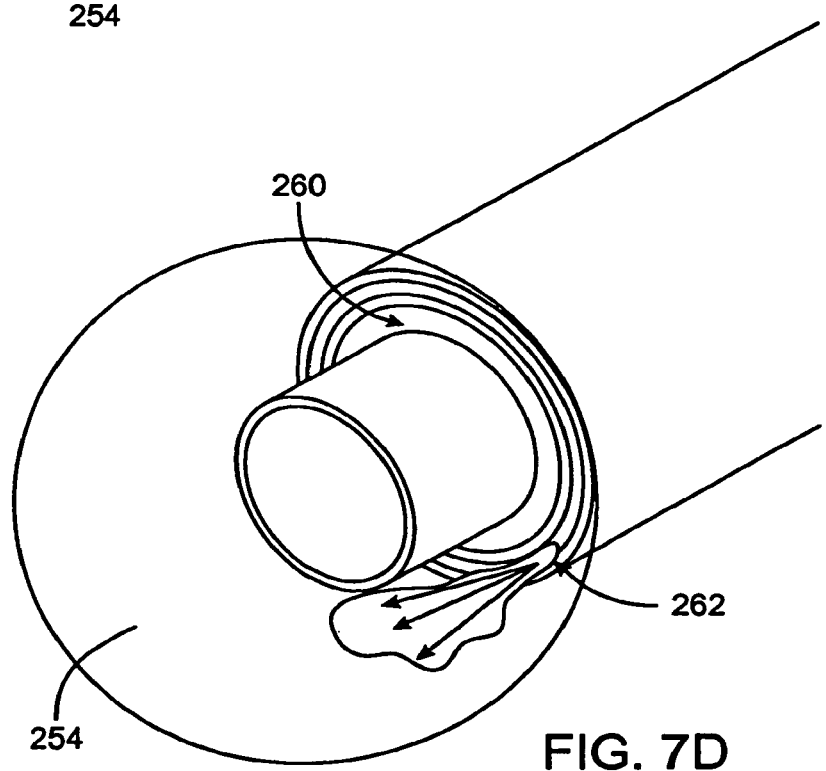
FIG. 7D is an enlarged view of the distal end of the device of FIG. 7C, shown with the optical viewing scope in position within an optically transparent balloon.

Referring now to FIGS. 7C and 7D, in many instances it will be preferable to perform some or all of the interventional steps of the methods of the present invention under direct optical viewing. One apparatus for performing such direct optical viewing is the bubble scope 250 illustrated in FIGS. 7C and 7D. The scope 250 includes a sheath 252, an inflatable, optically transparent balloon 254 at a distal end of the sheath, a fiberoptic scope 256, an inflation tube or lumen 258, a scope seal 260, and an inflation port 262 open to the interior of the balloon 254. Scope 256 is advanced distally through a lumen of the sheath 252 so that the scope extends through the seal 260, as illustrated in FIG. 7D. The seal around the scope permits inflation of the balloon through the inflation lumen, with an optically transparent medium entering through the inflation port 262. The optically transparent balloon 254 is preferably formed from an elastic material so that it can be engaged against the valve annulus or other interior cardiac surface and conform against said surface clip applier and other tools used in performing the methods of the present invention. Once in place inside the heart chamber, such as the left atrium above the mitral valve, the balloon 254 may be engaged against a surface to be treated, against the distal end of the clip applier or both. The bubble scope 250 may thus be used to initially position the clip applier, optionally to observe the delivery of the clip, and finally to observe clip placement to confirm it is proper.

Figure 11:
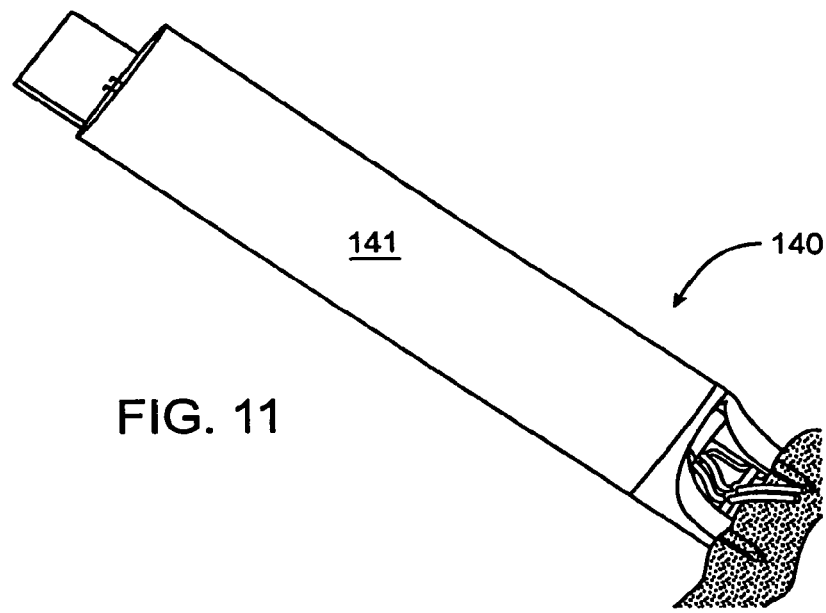
FIG. 11 is a perspective view of a distal end of a surgical device according to one embodiment of the present invention.

Referring now to FIG. 11, a distal end 140 of a surgical stapling device 141 for repair of cardiovascular valves is shown. As mentioned above, distal end 140 may have any of a variety of configurations, shapes, sizes, functions and the like in various embodiments of the invention. The following description, therefore, is provided for exemplary purposes only, to help describe one embodiment of a surgical device, and should not be interpreted to limit the scope of the invention as it is set forth in the claims.

Figure 11A:
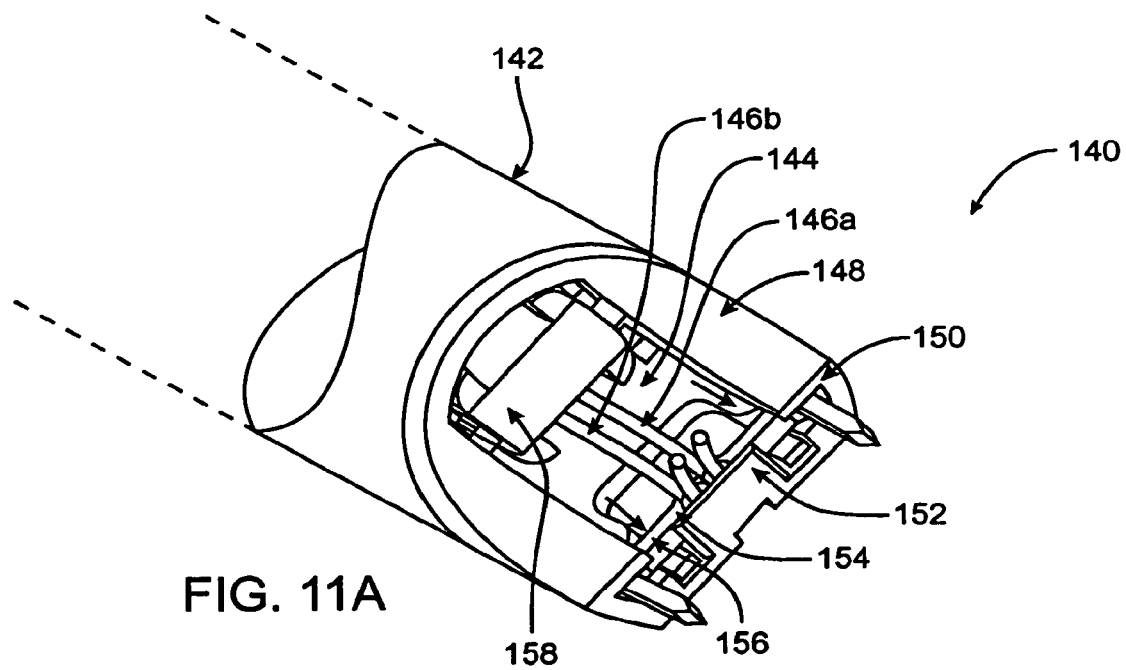
FIG. 11A is a close-up view of the distal end assembly of the device shown in FIG. 11.

That being said, and with reference now to FIG. 11A, one embodiment of a distal end assembly 140 suitably includes a distal end portion of shaft 142, an anvil 144, a tether 146 having parallel segments 146a and 146b, a nose piece 148, guide slots 150, a staple mandrel 152, a leaf spring 154, one or more staples 156, and a retainer belt 158. Again, other embodiments may include fewer or additional elements. Also, for the purposes of this description the terms "staple" and "clip" are interchangeable and generally refer to any fastener, anchor, or piece that may be attached to a valve. Generally, the features shown in FIG. 11A may be used to apply a plurality of staples 156, tethered with one or more tethers or cables 146, to a valve annulus. Tether 146 may include but is not limited to a strip, band, filament, wire, strap or any other connective element. In one embodiment, staples 156 are applied along the annulus of the a heart valve. One or more tethers 146 is pre-threaded through the eyelet (or eyelets) of each staple 156 and runs from the distal end assembly of device 140 to the its proximal end.

Once staples 156 are secured to the tissue, tether 146 is pulled from the proximal end of device 140 to cinch staples 156 and thereby reduce the annular diameter. Tension may be adjusted on tether 146 while using ultrasound Doppler flow guidance or direct visualization in real time to allow the annulus to expand for precise adjustment of the annular correction. After an optimal size of the annulus is achieved, one or more final staples are dispensed and crimped (using crimp bar 184 described with reference to FIG. 20) by the device. This step locks the tether 146 tension by securing the tether 146 to the final staple(s) 156. The tether 146 is then cut at the point beyond the last staple by a sliding blade 190 (FIG. 20) within the device or by any other suitable means. Shaft 142, with nose piece 148 and guide slots 15, acts to longitudinally guide staples 156 toward the distal end assembly of device 140 to be applied to a valve annulus. Anvil 144 pushes staples 156 forward/distally to be dispensed.

Figure 12:
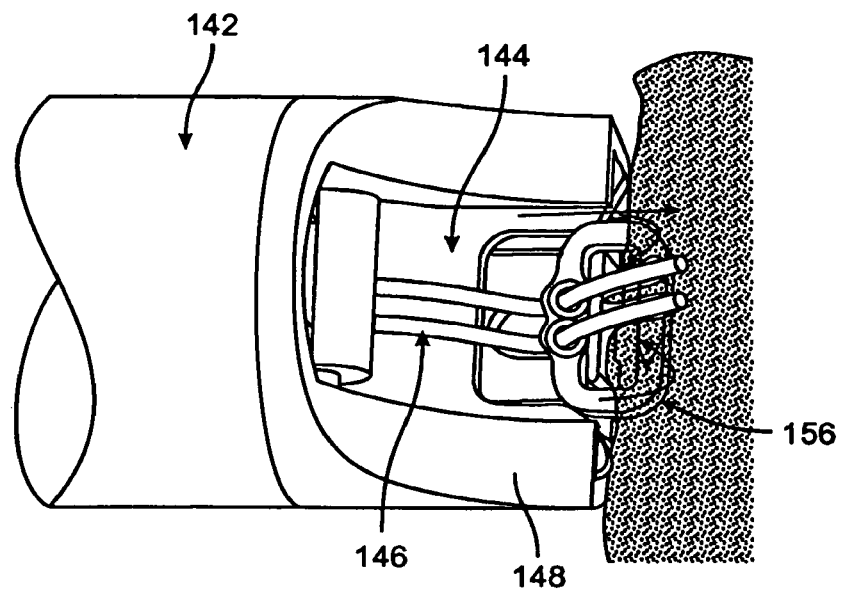
FIG. 12 is a perspective view of a distal end assembly of a surgical device in the process of closing a clip, according to one embodiment of the present invention.
Figure 12A:
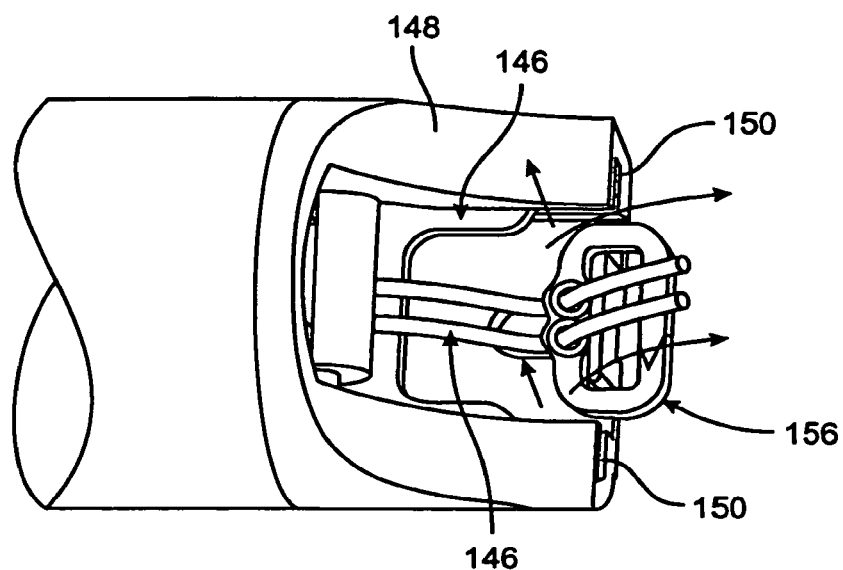
FIG. 12A is a perspective view of a distal end assembly as in FIG. 12, shown after closing the clip and in the process of retracting according to one embodiment of the present invention.

Referring now to FIG. 12, a perspective view of distal end assembly 140 is shown in the process of closing a clip 156, with anvil 144 pushing clip 156 forward. FIG. 12A then shows distal end assembly 142 after clip 156 is closed, with anvil 144 in the process of retracting. Generally, guide slots (not shown) along the length of the surgical device are continuous with the ramps and guide slots 150 in nose piece 148. In operation, a user activates an proximal actuator (not shown) which drives a ratchet to rotate retainer belt 158 (FIG. 15) such that a surface containing the set of staples translates distally. This activation of actuator also pushes anvil 144 distally.

Figure 13:
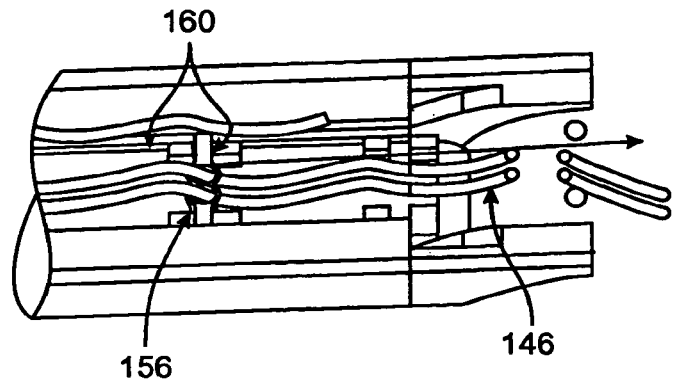
FIG. 13 is a top, sectional view of a distal end assembly of a surgical device in the process of advancing a clip, according to one embodiment of the present invention.
Figure 14:
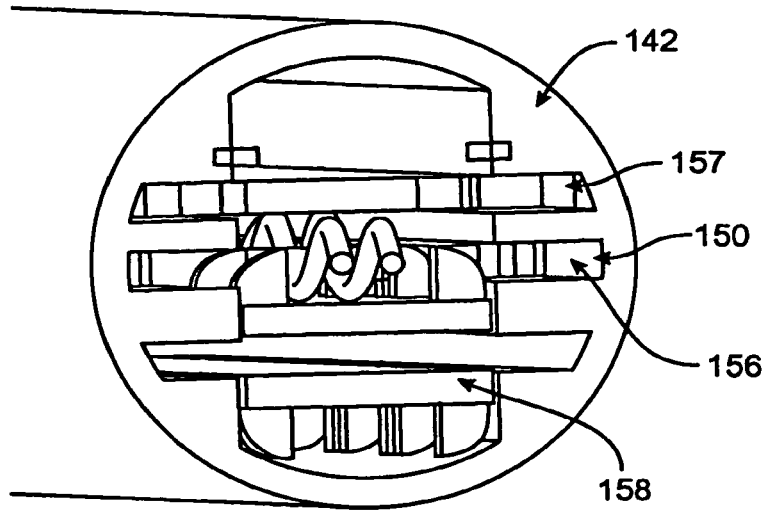
FIG. 14 is a transverse sectional view of a portion of a distal end assembly of a surgical device, according to one embodiment of the present invention.

Referring now to FIGS. 13 and 13A, retainer bumps 160 on retainer belt 158 contact generally fit around staples 156 and function to keep staples 156 in position while moving the staples distally. As the belt advances during the actuation process, staples 156 are guided forward by the guide slots 150 on each side of the inner diameter of the devices guide shaft 157.

Figure 15:
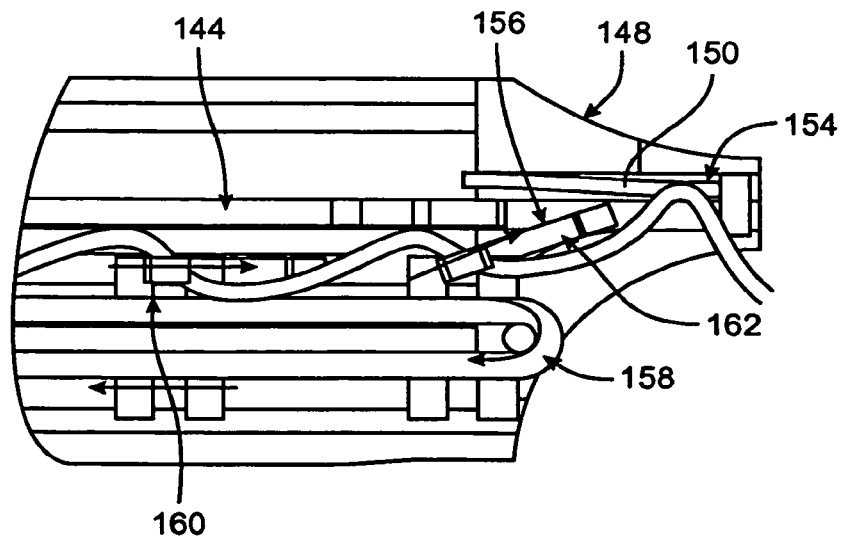
FIG. 15 is a side, sectional view of a distal end assembly of a surgical device in the process of dispensing a clip from a retainer of the device into a nose piece of the device, according to one embodiment of the present invention.
Figure 16:
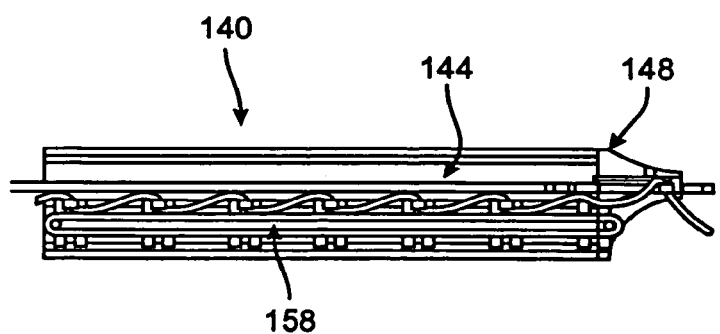
FIG. 16 is a side, sectional view of a portion of a distal end assembly of a surgical device showing multiple clips in the retainer of the device, according to one embodiment of the present invention.

Referring to FIG. 15, the most distal staple 156 moves to the distal end, up a ramp 162, and is dispensed into guide slots 150 in nose piece 148 which are in continuity with the ramp and the guide slots in the device shaft.

Once the distal staple 156 is moved into nose piece 148, anvil 144 moves forward (or distally) to move staple 156 distally until it bumps against staple mandrel 152 on the distal end of nose piece 148 (FIG. 11A). Leaf spring 154 generally pushes upward level with the top of staple mandrel 152, but when an unclosed staple slides over them, leaf springs 154 are deflected downward away from the top of staple mandrel 152. Staple 156 is retained within the plane of guide slots 150 in nose piece 148. In one embodiment, the inner surface of the distal end of anvil 144 is U shaped and the inner surfaces of the lateral prongs are curved outward. These outwardly curved lateral prongs act as ramps for the proximal-lateral aspect of staple 156. As anvil 144 is advanced, the prongs can ramp over the lateral surfaces of the staple legs distally as well as inwardly (FIGS. 12 and 12A). The prongs bend the outer staple legs around the staple mandrel resulting in a closed staple as shown in FIGS. 12 and 12A. Once staple 156 is closed, its lateral surfaces are not captured by the outside guide slot so it is and the staple is free to translate move transversely. As shown in FIG. 12A, anvil 144 retracts when an actuation lever is released, and the leaf springs push staple 156 up and out over staple mandrel 152.

Figure 17:
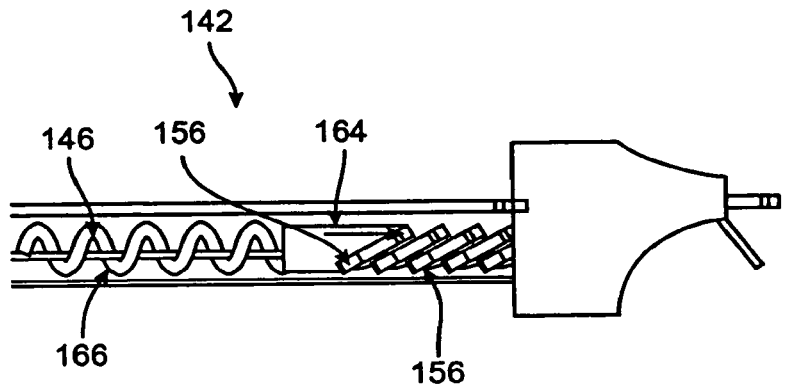
FIG. 17 is a side view of the inside of the shaft of a distal end assembly of a surgical device showing a longitudinally stacked clip design, according to one embodiment of the present invention.
Figure 18:
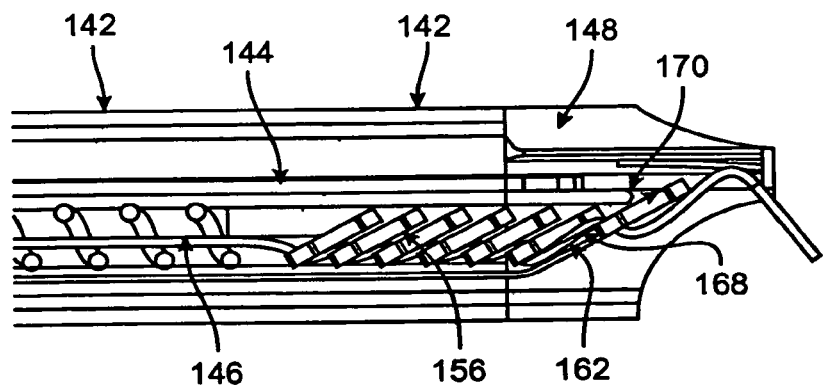
FIG. 18 is a side view of the inside of the shaft of a distal end assembly of a surgical device showing a longitudinally stacked clip design, according to one embodiment of the present invention.
Figure 19:
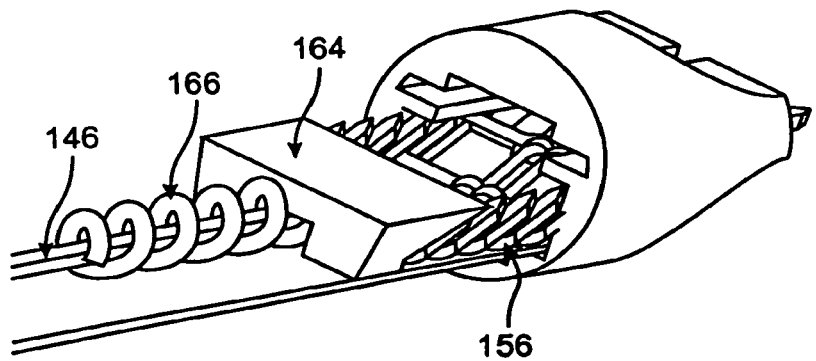
FIG. 19 is a perspective view of the inside of the shaft of a distal end assembly of a surgical device showing a longitudinally stacked clip design, according to one embodiment of the present invention.

In one embodiment, as shown in FIGS. 17-19, staples 156 are stacked longitudinally inside shaft 142. A compression spring 166 pushes on a compression bloc 164 to advance staples 156 forward as they are dispensed. The most distal staple 156 is pushed through a staple dispensing opening 170 (FIG. 18) by a staple dispensing push plate 168.

Figure 20:
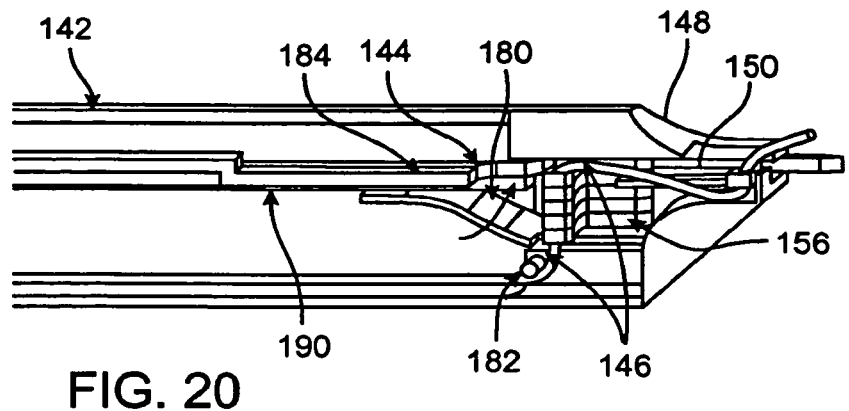
FIG. 20 is a perspective view of a distal end assembly of a surgical device showing a transversely stacked clip design, according to one embodiment of the present invention.
Figure 21:
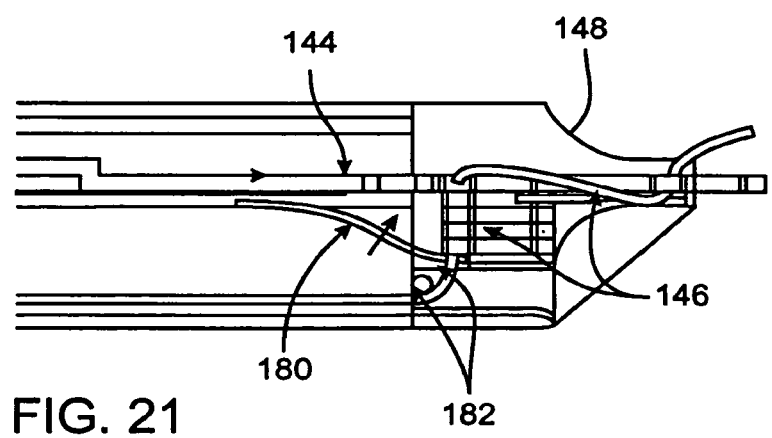
FIG. 21 is a side, sectional view of a distal end assembly of a surgical device showing a transversely stacked clip design, according to one embodiment of the present invention.
Figure 22:
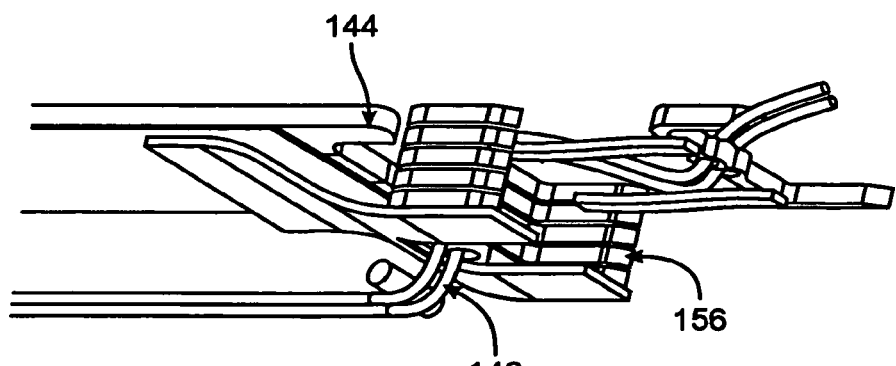
FIG. 22 is a perspective view of the inside of the shaft of a distal end assembly of a surgical device showing a transversely stacked clip design, according to one embodiment of the present invention.

In another embodiment, as shown in FIGS. 20-22, staples 156 are stacked transversely. Staple guide slots 150 in the nose piece 148 allow one staple 156 to be pushed from the staple stack at a time. As the staples are used up, the stack decreases in height. A staple stack spring 180 maintains staples 156 in position. Tether 146 is threaded through the eyelets of staples 156 and wraps around a cable pulley 182 so it can slide freely longitudinally as well as transversely through the stack of staples 156. Free cable motion is important for making fine adjustments of cable tension through staples 156 once they have been delivered to tissue. The free sliding of the cables through the undispensed staples also allows for newly dispensed staples to slide freely in position to be stapled to the tissue.

Figure 23:
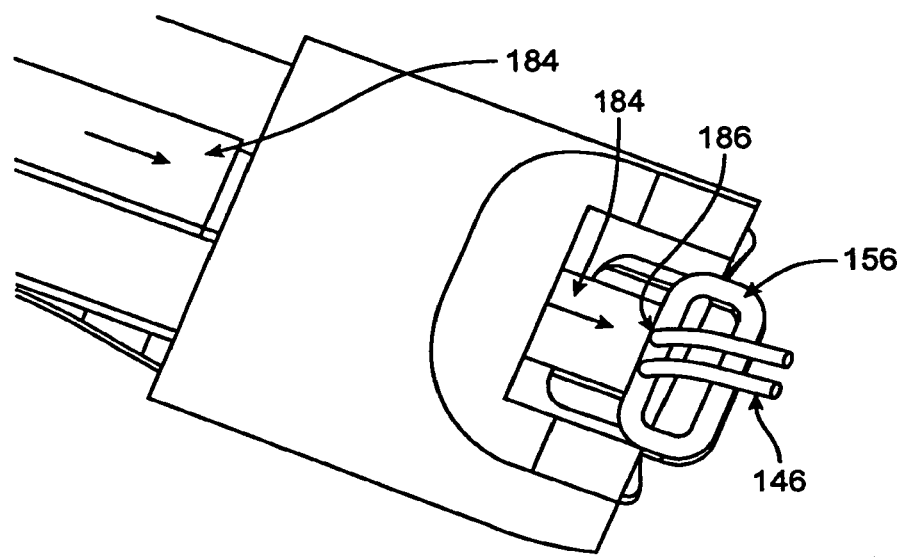
FIG. 23 is a perspective view of a distal end assembly of a surgical device showing a clip crimping feature of the device, according to one embodiment of the present invention.

Referring now to FIG. 23, after staples 156 other than one or more final staples have been secured to tissue and cable tension and position have been adjusted (if necessary), one or more final staples 156 are then dispensed and stapled to the tissue. In addition to bending the legs of the final staples 156 inward to secure the final staples 156 to annulus tissue, in one embodiment the eyelets of the final staples are crimped down to secure cable 146 to the final staples 156. This crimping may be achieved by a crimp bar 184, as shown in FIG. 23, which may be advanced forward (distally) to apply pressure against eyelets 186 (or "holes") of a clip. The pressure applied by crimp bar 184 closes eyelets 186 to a degree sufficient to secure tether 146 within eyelets 186, thus securing staple 156 to tether. In some embodiments, crimp bar 184 is fitted within a central slot in anvil 144. In closing the legs of non-termination staples, crimp bar 184 is retracted in the central slot. To attach a final staples 156, a user activates a proximal actuator which drives crimp bar 184 to protrude forward. Alternatively, the switch may also be self-activated by the device when the final staple (or staples) is ready to be secured to tissue. When anvil 144 advances to close the legs, the protruding crimp bar 184 presses staple eyelets 186 against the staple mandrel to crimp it tight on the cable to lock the cable to the staple.

Figure 24:
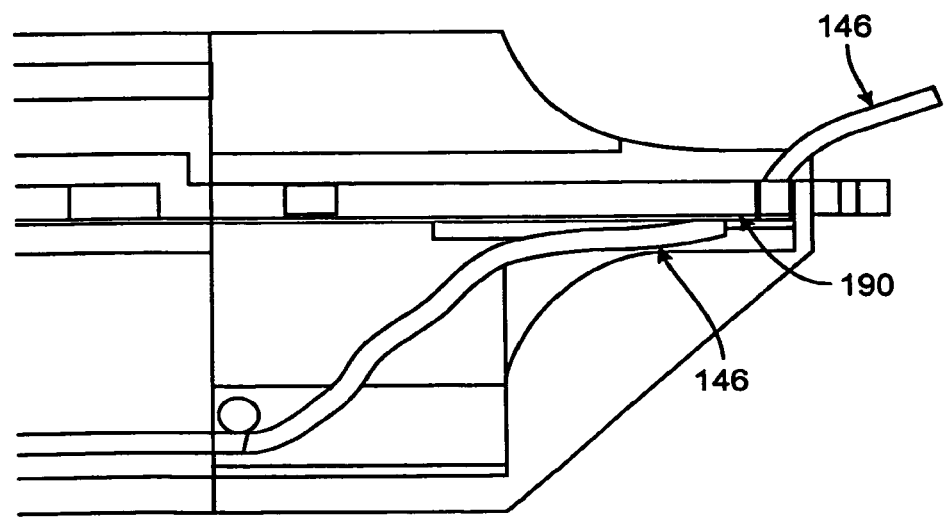
FIG. 24 is a side view of a distal end assembly of a surgical device showing a tether cutting feature of the device, according to one embodiment of the present invention.

With reference now to FIG. 24, some embodiments of the device include a cable cutter 190 for cutting tether or cable 146 —once it is cinched to reduce the diameter of the valve. In some embodiments, once the final staple 156 is applied, tension is applied to cable and staple eyelets are crimped, a switch (e.g., crank 304 in FIG. 25) is activated to drive a spring loaded tether cutter 190 forward to cut cable 146. In other embodiments, a user may manually activate cutter 190. Generally, any suitable means for cutting cable 146 may be used in the present invention.

The various features of distal end assembly 140 described above may be made from any suitable materials and combinations of materials. For example, nose piece 148 and housing 142, in one embodiment, may be made from materials such as but not limited to stiff polymers such as polycarbonate, nylon, acrylonitrile butadiene styrene (ABS), polypropylene, PEEK, PVDF or urethane. In another embodiment, nose piece 148 may be made from one or more stainless steel materials such as 17-4, 304, or 316 steel. Staple mandrel 152, anvil 144, crimp bar 184, and cutter 190 in one embodiment are made from a hard stainless steel such as hardened 17-4 steel and/or 440 steel. Alternatively, these features may be made from tungsten carbide or any other suitable material, such as softer stainless steels coated with titanium nitride to increase surface hardness. Leaf springs 154 and compression springs 166 in one embodiment may be made from a polymer like PEEK, nickel titanium, or stainless steel, but other materials may alternatively be used. Staple retainer belt 158 may be made out of flexible polymers such as high flex PVDF, PTFE, nylons, polyethylene, polyurethane, polyester, isoprene, silicones and/or the like. Generally, any of these materials, combinations of these materials, or any other suitable materials or combinations not mentioned here may be used to manufacture one or more of the elements of a surgical device for repairing cardiovascular valves according to the invention.

An exemplary stapling device 141 is illustrated in FIG. 25 where the shaft 142 is connected to a pistol grip handle assembly 300. The assembly 300 includes a trigger 302 for advancing and deploying individual clips 156 and optionally a crank 304 for actuating the tether cutter 190 (FIG. 24). Of particular interest, a tether tensioning mechanism 310 may be provided to take-up the tether segments 146a and 146b, as best seen in FIG. 26. The tensioning mechanism includes a spool 312 which is mounted to spin freely to release tether 146 as the device dispenses the tether as the staples 156 are deployed. When desired, however, the mechanism can be switched to permit the tether 146 to be "reeled" back over the spool 312 to pull back and tension the deployed tether, i.e., to apply a constricting force to the staples surrounding the valve annulus. Usually, the mechanism will have a ratchet (not shown) to assist in manually turning of the spool 312 to reel in the tether, and optionally the mechanism will include a tension control or measurement mechanism (not shown). Thus, immediately prior to crimping a terminal clip, the tether 146 can be cinched to a preselected tension with the tensioning mechanism.

Although the foregoing is a complete and accurate description of the present invention, it should be emphasized that the description provided above is for exemplary purposes only that variations may be made to the embodiments described without departing from the scope of the invention. For example, various embodiments of the invention may be used to repair a valve other than the mitral valve, such as the tricuspid valve. In other embodiments, clips may be eliminated and a rotatory cord such as a suture alone may be used. Other embodiments may include only a single, larger clip or fastener. Thus, the above description should not be construed to limit the scope of the invention as described in the appended claims.

What is claimed is:

1. A system comprising:
a device for applying tethered clips to an annulus, the device comprising:
 a shaft having a proximal end and a distal end;
 a plurality of clips slidably coupled to a tether, the tethered clips delivered by the shaft;
 a clip applier at or near the distal end of the shaft for securing the clips to the annulus; and
 at least one actuator at or near the proximal end of the shaft for causing the device to advance the clips and for activating the clip applier to secure the clips to the annulus; and
a stabilization device comprising a pair of rings which are adapted to clamp opposed faces of the annular surface.

2. A device as in claim 1, wherein the clip applier comprises:
 a pusher coupled with the actuator for advancing the clips; and
 at least one slot in an inner surface of the shaft for guiding the clips.

3. A device as in claim 1, wherein the at least one actuator is selected from the group consisting of a trigger, a handle, a plunger, a squeeze-activated device, a syringe-grip device and a foot-operated device.

4. A device as in claim 1, wherein each of the plurality of clips includes at least one eyelet, and the tether passes through the at least one eyelet of each clip.

5. A device as in claim 1, wherein the shaft is introducible into a patient through a minimally invasive incision.

6. A device as in claim 1, wherein the tether is selected from the group consisting of a suture material, a Teflon strip, a band, a filament, a wire and a strap.

7. A system as in claim 1, wherein the device is adapted to clam over and under a heart valve annulus.

* * * * *